United States Patent [19]
Archer et al.

[11] Patent Number: 5,997,843
[45] Date of Patent: *Dec. 7, 1999

[54] RADIOMETAL COMPLEXES THAT LOCALISE IN HYPOXIC TISSUE

[75] Inventors: Colin Mill Archer, Chesham; James Frederick Burke, Amersham; Lewis Reuben Canning, Chesham; Barbara Edwards, Hardwick; Adam Charles King, Aylesbury, all of United Kingdom

[73] Assignee: Amersham International PLC, Buckinghamshire, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/591,519

[22] PCT Filed: Aug. 3, 1994

[86] PCT No.: PCT/GB94/01705

§ 371 Date: Apr. 9, 1996

§ 102(e) Date: Apr. 9, 1996

[87] PCT Pub. No.: WO95/04552

PCT Pub. Date: Feb. 16, 1995

[30] Foreign Application Priority Data

Aug. 4, 1993 [GB] United Kingdom ................. 93306220

[51] Int. Cl.$^6$ ............................... A61K 51/04; C07F 5/00
[52] U.S. Cl. ............................................ 424/1.65; 534/14
[58] Field of Search ................................ 424/1.65, 1.69; 534/14, 15, 16, 10, 11, 12, 13

[56] References Cited

U.S. PATENT DOCUMENTS

| | | | |
|---|---|---|---|
| 4,615,876 | 10/1986 | Troutner | 424/1.11 |
| 4,789,736 | 12/1988 | Canning et al. | 534/14 |
| 4,818,813 | 4/1989 | Nowotnik et al. | 534/14 |
| 5,116,598 | 5/1992 | Nosco | 424/1.11 |
| 5,302,370 | 4/1994 | Neumeier et al. | 424/1.53 |
| 5,387,692 | 2/1995 | Riley et al. | 548/313.7 |
| 5,401,490 | 3/1995 | Wiebe et al. | 424/1.73 |
| 5,457,183 | 10/1995 | Sessler et al. | 534/11 |
| 5,589,576 | 12/1996 | Archer et al. | 534/14 |

FOREIGN PATENT DOCUMENTS

| | | |
|---|---|---|
| 0 123 504 | 10/1984 | European Pat. Off. . |
| 0 171 984 | 2/1986 | European Pat. Off. . |
| 0 179 608 | 4/1986 | European Pat. Off. . |
| 0 380 016 | 8/1990 | European Pat. Off. . |
| 0 417 870 | 3/1991 | European Pat. Off. . |
| 0 544 412 | 6/1993 | European Pat. Off. . |

OTHER PUBLICATIONS

39th Annual Meeting of the Society of Nuclear Medicine, Los Angeles, California, USA, Jun. 9–12, 1992. Di Rocco R.J. et al., "Imaging Regional Hypoxia with a New Technetium–Labeled Imaging Agent in Rabbit Myocardium after Occlusion of the Left Anterior Descending Coronary Artery," *J. Nucl. Med.*, vol. 33, No. 5 Suppl., p. 865, 1992, see Abstract 171.

J. Nucl Med, vol. 34, No. 6, pp. 885–888, US, 1993, Groshar D et al. 'Imaging tumor hypoxia and tumor perfusion', see p. 886, right column—p. 888, left column; table 1.

Int. J. Appl. Radiat. Isot., 1984, vol. 35, pp. 467–470, Troutner, David E. et al., 'A neutral lipophilic complex of technetium–99m with a multidentate amine oxime', see p. 467; figure 1.

Eur. J. Nucl. Med., 1984, vol. 9, pp. 511–516, Volkert, W.A. et al., '99mTc–propylene amine oxime (99mTC–PnAO); a potential brain radiopharmaceutical', see abstract; figures, * Results *.

Int. J. Nucl. Med. Biol., 1984, vol. 11, pp. 243–246, Volkert, W.A. et al., 'The behavior of neutral amine oxime chelates labeled with technetium at tracer level', see the whole document.

Nucl. Med. Biol., 1986, vol. 13, pp. 261–267, Chaplin, S.B. et al., 'Regional cerebral uptake and retention of technetium–99m–tetramethyl– and pentamethyl–propyleneamine oxime chelates', *Materials and Methods *, see tables.

Clin. Nucl. Med. (US), 1990, vol. 15, No. 3, pp. 175–177, Fockele D.S. et al., 'Tc–99m HMPAO SPECT of the brain in the neonate', see abstract; figures.

J Nucl Med (United States), vol. 34, No. 3, pp. 405–411, 1993, Moore RB et al., 'Measurement of PDT–induced hypoxia in Dunning prostate tumors by iodine–123–iodoazomycin arabinoside [see comments]', see abstract; figures; tables; * Discussion *.

J. Chem. Soc., Chem. Commun. (GB), 1991, No. 17, pp. 1171–1173, Ware D.C. et al., 'Design and synthesis of cobalt (III) nitrogen mustard complexes as hypoxia selective cytotoxins. The X–ray crystal structure of bis(3–chloropentane–2, 4–dionato)(RS–N,N' bis (2–chloroethyl)ethylenediamine) cobalt (III) perchlorate, (Co(Clacac)2(bce)C104, see p. 1171.

Database WPI, Derwent Publications Ltd., London, GB; AN 84–072822[12] & RO,A,82 684 (INST FIZ ING NUCL) Sep. 30, 1983, see abstract.

Anticancer Res. (GR), 1988, vol. 8, No. 4, pp. 681–684, Ilchul Kim S. et al., 'A new look at radionuclides therapy in metastatic disease of bone (review and prospects)' see abstract, see p. 683.

Biochem. Biophys. Res. Commun., 1993, vol. 193, No. 3, pp. 1239–1246, Rumsey W.L. et al., 'A novel technetium–99m–labeled nitroheterocycle capable of identification of hypoxia in heart', see discussion, see figures.

(List continued on next page.)

*Primary Examiner*—Jose' G. Dees
*Assistant Examiner*—Michael G. Hartley
*Attorney, Agent, or Firm*—Marshall, O'Toole, Gerstein, Murray & Borun

[57] ABSTRACT

Methods of imaging and radiotherapy of hypoxic tissues are provided using radiometal complexes not substituted by a hypoxia-localizing moiety.

16 Claims, 3 Drawing Sheets

OTHER PUBLICATIONS

39th Annual Meeting of the Society of Nuclear Medicine, Los Angeles, California, USA, Jun. 9–12, 1992. Linder K.E. et al., 'Chemistry of a Technetium–PNAO–Nitromidazole Complex that Localizes in Hypoxic Tissue'& J. Nucl. Med., vol. 33, No. 5 Suppl., pp. 919, 1992, see Abstract No. 400.

39th Annual Meeting of the Society of Nuclear Medicine, Los Angeles, California, USA, Jun. 9–12, 1992. Di Rocco R.J. et al., 'Imaging Regional Hypoxia with a New Technetium–Labeled Imaging Agent in Rabbit Myocardium After Occlusion of the Left Anterior Descending Coronary Artery' & J. Nucl. Med., vol. 33, No. 5 Suppl., pp. 865, 1992. see Abstract 171.

J. Med. Chem., 1994, vol. 37, No. 1, pp. 9–17, Linder K.E. et al., 'TcO(PnAO–1–(2–nitroimidazole))[BMS–181321], a new technetium–containing nitroimidazole complex for imaging hypoxia: synthesis, characterization, and xanthine oxidase–catalyzed reduction', see the whole document.

RADIOMETAL COMPLEXES THAT LOCALISE IN HYPOXIC TISSUE

This application is a 371 of PCT/GB94/01705, filed Aug. 3, 1994.

PRIOR ART DISCUSSION

1 Ligand Systems

U.S. Pat. No. 4,615,876 discloses neutral technetium complexes of diaminedioxime (or bis aminooxime) ligands having 2 to 4 carbons in the bridging group. The emphasis is on PnAO which forms stable, relatively lipophilic technetium complexes. PnAO analogues and derivatives are disclosed for various radiopharmaceutical applications including brain imaging and myocardial metabolism studies (using PnAO-fatty acid conjugates). The only butylene-bridged ligand complex prepared was the parent Tc-BnAO which was shown to be neutral, stable and less lipophilic than Tc-PnAO.

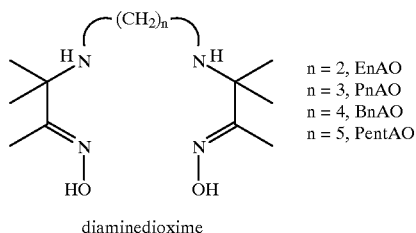

n = 2, EnAO
n = 3, PnAO
n = 4, BnAO
n = 5, PentAO diaminedioxime

Volkert et al.[1] (1984) studied the radiolabelling and rat biodistribution of the $^{99m}$Tc complexes of EnAO, PnAO and BnAO. $^{99m}$Tc-BnAO was found to exhibit insignificant brain uptake (0.12% injected dose at 30 sec pi) whereas with Tc-EnAO and Tc-PnAO the figures are 0.74% and 1.3% respectively. Consequently subsequent radiopharmaceutical development focused on PnAO ligands and desmethylated PnAO analogues have been patented as technetium brain imaging agents (U.S. Pat. No. 4,789,736 and U.S. Pat. No. 4,818,813).

Budsky et al.[2] (1990) outline a synthesis of the BnAO analogue shown (n=4). Therefore, despite the fact that Tc-BnAO was first disclosed in 1984, no radiopharmaceutical applications for this ligand system have been described.

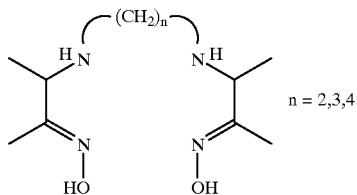

n = 2,3,4

Jurisson et al.[3] (1987) characterised the technetium complexes of a series of diaminedioxime ligands with n=2 to 5. X-ray crystal structures of the $^{99}$Tc complexes confirmed that both EnAO and PnAO[4] give technetium complexes with a Tc(V) monoxo core, whereas PentAO has a Tc(V) dioxo core. $^{99}$Tc-BnAO was not crystallographically characterised, but infra-red data suggested a dioxo core.

Troutner et al.[5] (1986) disclosed the technetium complex of an EnAO analogue with expanded chelate rings, H$_2$dddo. The complex was found to be less lipophilic than Tc-PnAO.

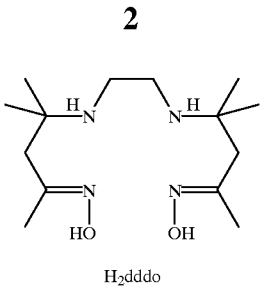

H$_2$dddo

2 Hypoxia Imaging

Radiopharmaceuticals which selectively concentrate in hypoxic cells are highly desirable since they could permit the diagnosis of potentially salvageable tissue which is at risk of infarction. Organs of interest for imaging would include heart and brain. Certain tumours are also known to be hypoxic, hence a hypoxia-specific radiopharmaceutical could also be used for the diagnosis and radiotherapy of tumours. It is also believed that hypoxia-selective radiopharmaceuticals could be useful for the detection of peripheral vascular disease.

Various nitro-heteroaromatic compounds including radiosensitisers such as misonidazole are known to be trapped in hypoxic cells. Preferred examples are 2-nitroimidazoles. $^{18}$F-radiolabelled and radioiodinated misonidazole analogues have been described for hypoxia imaging and include $^{123}$I-iodoazomycin arabinoside (IAZA)[6,7] and $^{18}$F-misonidazole[8].

The preferred isotope for radiopharmaceutical imaging is $^{99m}$Tc by virtue of both its availability and imaging characteristics. Prior art attempts to design a radiometal (e.g. $^{99m}$Tc, $^{186}$Re or $^{188}$Re) hypoxia agent were based on a conjugate of a radiometal ligand and a hypoxia-localising moiety, such as a nitroimidazole.

Thus EP 417870 claims nitroimidazole conjugates of diaminediphenol and PnAO ligands. A $^{99m}$Tc complex of a diaminediphenol-nitroimidazole conjugate is disclosed which has a hypoxic/oxic ratio of 2:8 in an in vitro cell model. EP 441491 A1 discloses boron-capped tris (dioxime) "BATO" technetium complexes in which the boronic acid moiety is functionalised with a nitroheteroaromatic hypoxia-localising moiety.

EP 544412 A2 claims a range of diaminedioxime (n=2–5) and N$_2$S$_2$ diaminedithiol ligands functionalised with at least one hypoxia-localising moiety. Such hypoxia localising groups are described in detail on pages 7–10 and claims 18–22 of the application. The localising groups described encompass a wide range of nitroheterocycles. The supporting Examples are limited to 2 particular ligand systems—PnAO and BAT, but several 2- and 4-nitroimidazole conjugates of these ligands are prepared. No examples of diaminedioximes other than PnAO are disclosed.

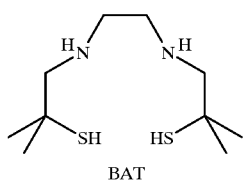

BAT

Indeed, pages 6 to 7 of EP 544412 envisage that the technetium complexes of such ligands will only have a monoxo core (Tc=O), when it is well known in the field that Tc-PentAO (n=5) has a dioxo core[3] and Tc-BnAO is believed to be similar[3]. The technetium complexes of the PnAO-nitroimidazoles described show modest hypoxia selectivity in a variety of in vitro screens.

U.S. Pat. No. 5,026,694 claims square planar platinum complexes containing at least one nitroheterocycle ligand (e.g. a nitroimidazole) as radiosensitizers. The idea of radio-labelling such complexes with $^{99}$Tc(sic), $^{131}$I or $^{111}$In for imaging hypoxic tumours is disclosed. For technetium or indium, however, this would clearly require a binuclear complex and is therefore no different in concept to other chelate-radiosensitizer conjugates.

U.S. Pat. No. 5,100,885 reveals that copper (II) complexes are known both as radiosensitizers and radioprotective drugs and that it is not possible to predict which mode of action will prevail. U.S. Pat. No. 5,100,885 discloses mixed ligand Cu(II) complexes of bipyridyl or phenanthroline with bidentate oxygen ligands such as diacids or diphenols as radiosensitizers. There is no suggestion of the use of radiometals for imaging and the complexes described are completely different from those claimed here.

THE INVENTION

This invention discloses a range of ligands which form radiometal complexes capable of localising selectively in hypoxic cells. The conventional approach to the design of radiometal (e.g. $^{99m}$Tc) hypoxia-targeting agents is simply to prepare chelate-conjugates of known hypoxia-localising or targeting moieties such as nitroheterocycles, especially nitroimidazoles. It is the surprising finding of this invention that certain ligand systems form radiometal complexes with the intrinsic property of localising in hypoxic cells, i.e. a conjugated targeting molecule (such as a nitroimidazole) is unnecessary. In addition these radiometal complexes, particularly of $^{99m}$Tc, have been shown to exhibit much higher selectivity for hypoxic cells than prior art complexes.

In one aspect this invention provides radiometal complexes for imaging or radiotherapy of hypoxic tissue. A radiometal complex is of a substituted or unsubstituted ligand, whereby such complex has the intrinsic property of localising in tumours or hypoxic tissue, and wherein the ligand is not substituted by any hypoxia-localising moiety. The ligand is preferably a diaminedioxime having the structure

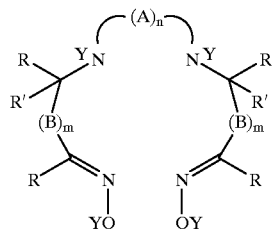

where n=2–5,
m=0, 1, 2,
Y is independently H or R,
R, R' are independently: H, $C_{1-10}$ linear or branched hydrocarbon which may be alkyl or one or more of alkenyl; alkoxy; alkoxyalkyl; primary, secondary or tertiary amide; primary, secondary or tertiary amine; carboxylic acid; hydroxyalkyl; aryl; heterocyclic; heteroaryl or two R groups taken together with the atom(s) to which they are attached form a carbocyclic, heterocyclic, saturated or unsaturated spiro or fused ring; or the two R groups of a $CR_2$ or CRR' group adjacent to a NR group may be combined to give one or more —CONR— amide groups, A and B are independently chosen and:
either each A and B is —$CR_2$—,
or AA and/or BB is —CR=CR—, —N=N—, —NR—NR— or —N=CR—,
or AAA is —$CR_2$—O—$CR_2$—, —$CR_2$—S—$CR_2$— or —$CR_2$—NR—$CR_2$—.

These complexes are usually neutral. The radiometal is preferably technetium, rhenium, rhodium or cobalt. For imaging purposes, the radiometal is preferably technetium-99m and the complex preferably has the formula [TcOL] where L is the ligand.

In another aspect the invention provides a complex having the intrinsic property of localising in tumours or hypoxic tissue, of a radiometal with a ligand having the structure

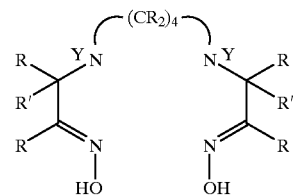

where at least one R is —A—$R^2$, where A is a linking group and $R^2$ is a hypoxia localising moiety,
Y is independently H or R,
and the other R and R' are independently: H, $C_{1-10}$ linear or branched hydrocarbon which may be alkyl or one or more of alkenyl; alkoxy; alkoxyalkyl; primary, secondary or tertiary amide; primary, secondary or tertiary amine; carboxylic acid; hydroxyalkyl; aryl; heterocyclic; heteroaryl or two R groups taken together with the atom(s) to which they are attached form a carbocyclic, heterocyclic, saturated or unsaturated spiro or fused ring; or the two R groups of a $CR_2$ or CRR' group adjacent to a NR group may be combined to give one or more —CONR— amide groups.

Although the complexes described have the intrinsic property of localising in tumours or hypoxic tissue, it is nevertheless possible to link the ligand to a hypoxia-localising moiety. In another aspect of the invention, certain of the ligands described, which may optionally be linked to a hypoxia localising moiety, are claimed as new compounds per se together with their radiometal complexes. Hypoxia-localising moieties, and techniques for linking them to metal-chelating moieties, are described in WO 94/08949 which is incorporated herein by reference.

In another aspect, the invention provides radio imaging kits comprising ligands as described, preferably with stannous reducing agent in a freeze-dried state, adapted on addition of $^{99m}$Tc pertechnetate to form a complex for radio imaging.

In yet another aspect, the invention provides a method for imaging or radiotherapy of hypoxic tissue of a patient which method comprises administering to the patient an effective amount of a complex as defined.

Figure 1A:
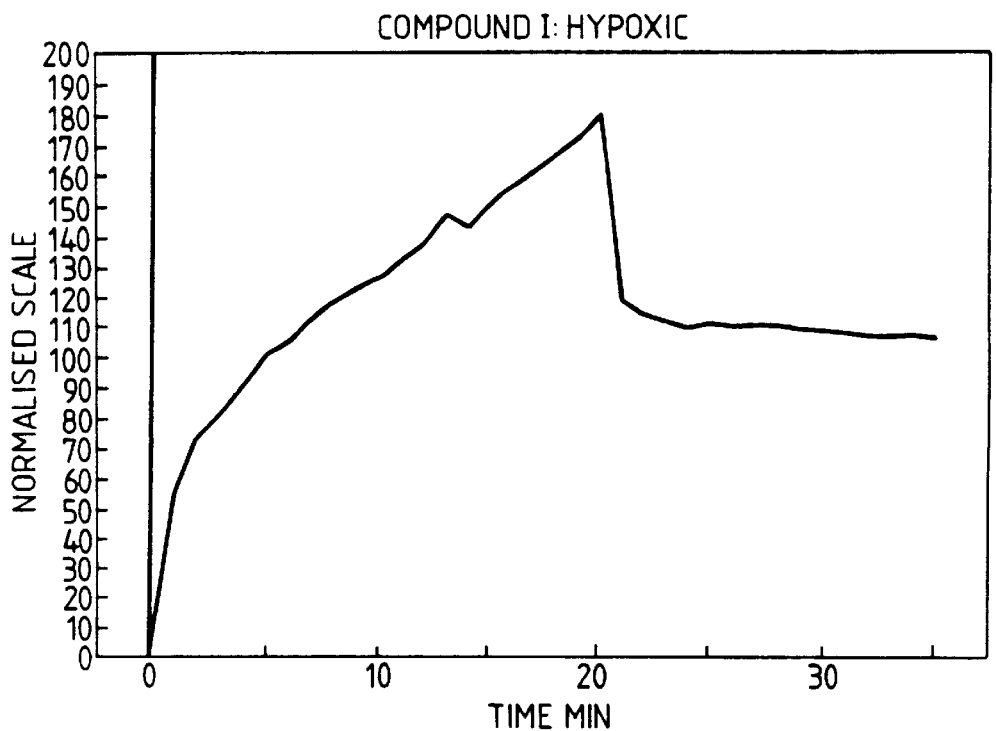
FIGS. 1A and 1B depict a comparison of Compound I between hypoxic and oxic conditions in an isolated perfused heart model.
Figure 1B:
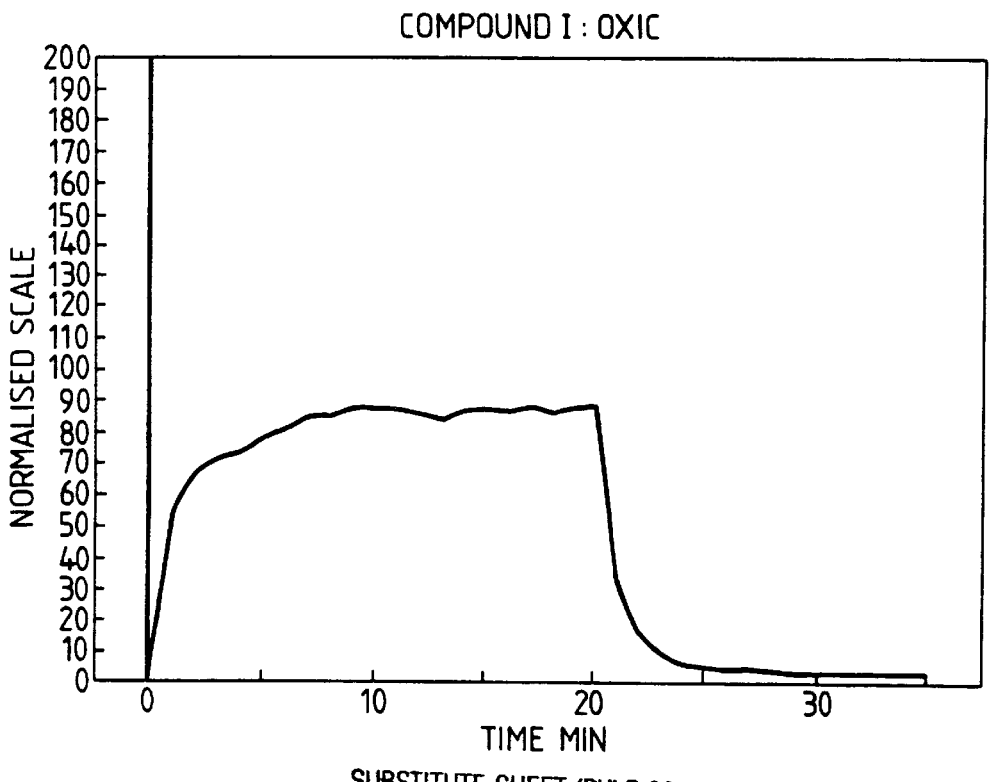
Figure 2A:
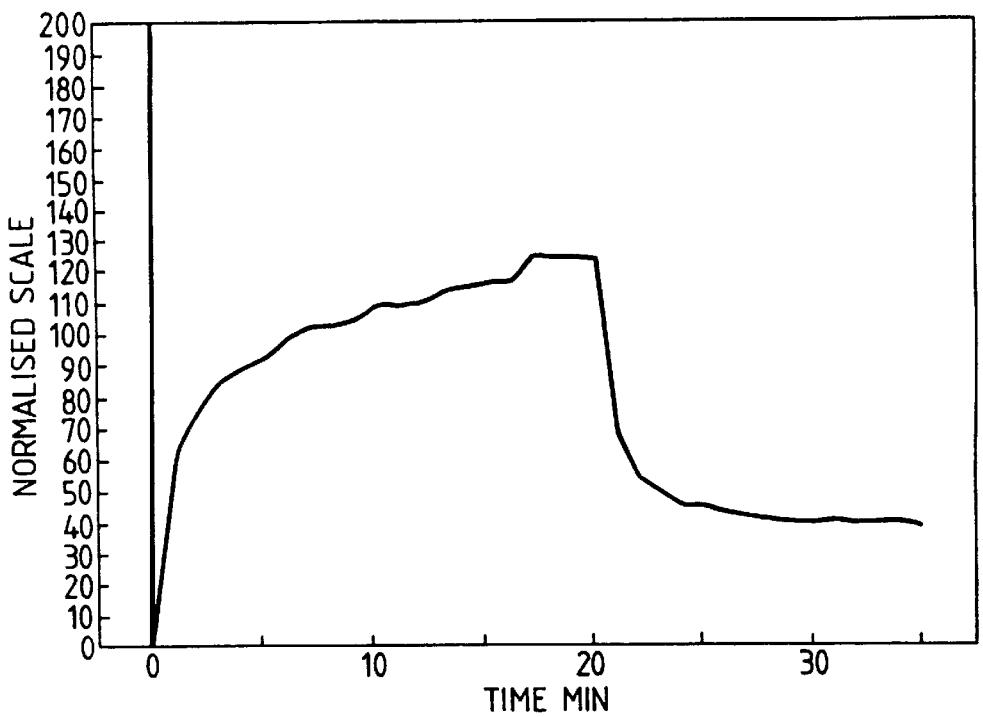
FIGS. 2A and 2B depict a comparison of Compound IV between hypoxic and oxic conditions in an isolated perfused heart model.
Figure 2B:
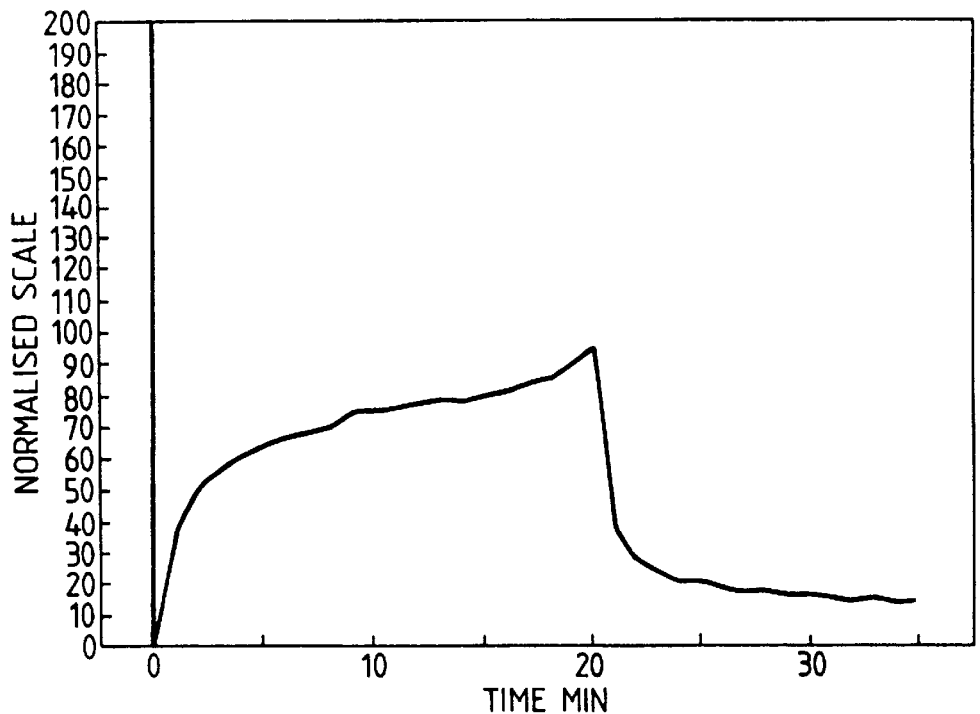
Figure 3A:
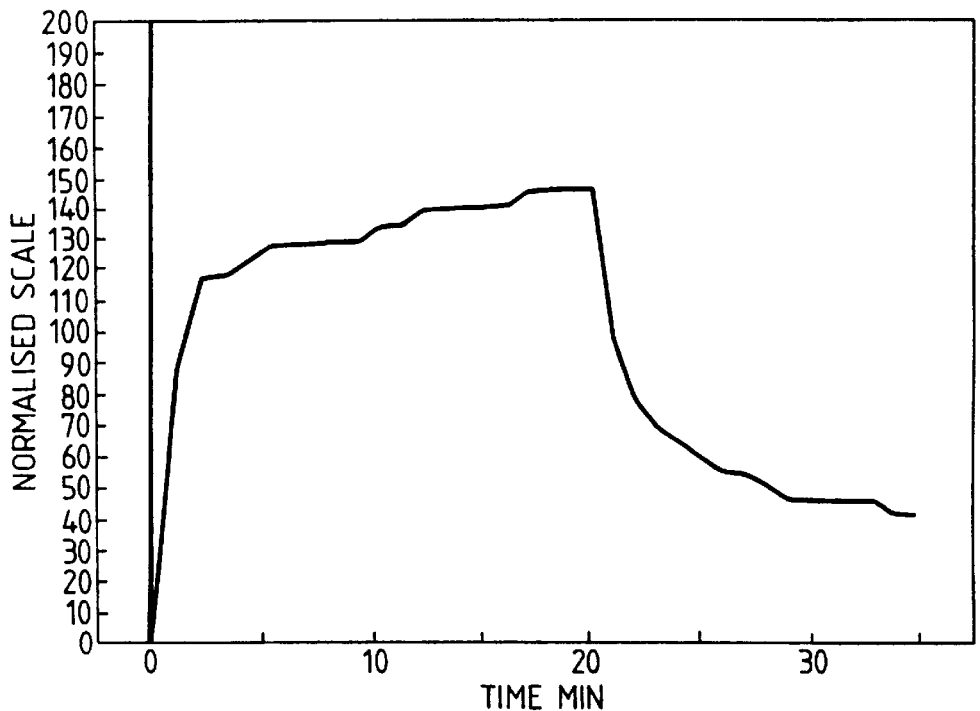
FIGS. 3A and 3B depict a comparison of $^{99m}$Tc-PnAO between hypoxic and oxic conditions in an isolated perfused heart model.
Figure 3B:
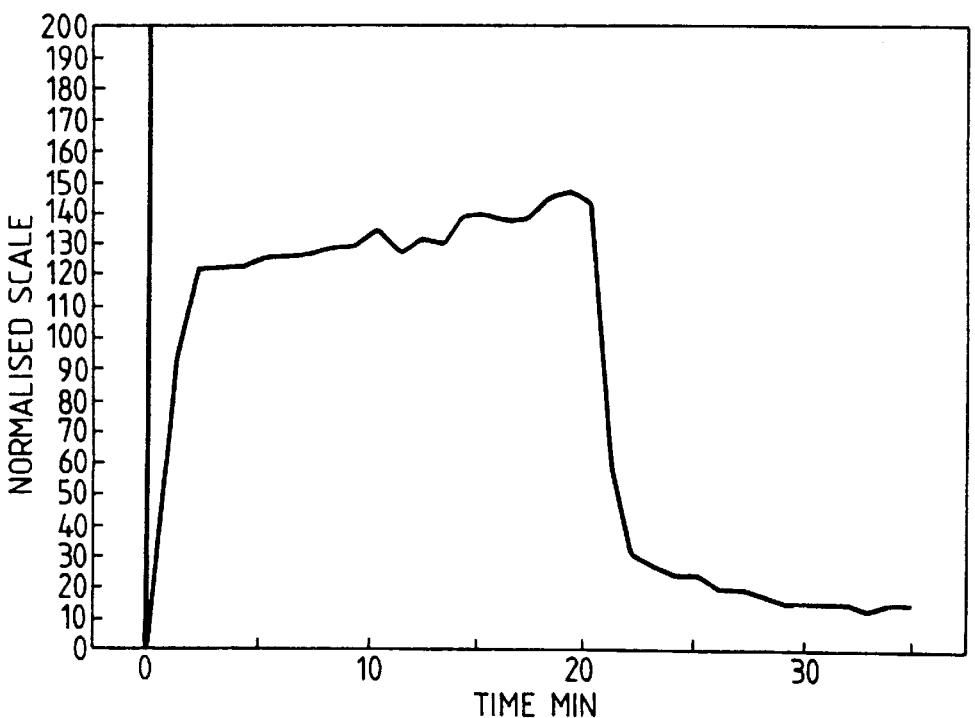

The hypoxic cell uptake experiments in an isolated perfused heart model (Example 21) indicate that much of the hypoxia selectivity of the prior art $^{99m}$Tc complex of Compound 5 is, in fact, due to the Tc-PnAO complex itself. This effect is seen more dramatically for the $^{99m}$Tc complex of Compound I (BnAO), which shows significantly greater hypoxic cell selectivity than the corresponding nitroimidazole conjugate, i.e. $^{99m}$Tc-Compound II. Introduction of a second nitroimidazole (Compound XI) only further reduces the hypoxia selectivity.

Comparison of $^{99m}$Tc compound VII and Compound XII shows that exchanging an ethyl group for the nitroimidazole ring has little or no effect on both the hypoxic/oxic ratio and normalised hypoxic retention.

Thus the nitroimidazole 'hypoxia-localising moiety' has minimal effect on the targeting of the radiometal complex since the intrinsic properties of the radiometal complex are predominantly responsible for the hypoxia selectivity. The differences which are observed with the nitroimidazole conjugates are probably largely attributable to simple alteration of the lipophilicity/hydrophilicity balance of the complex.

This invention demonstrates that certain radiometal complexes possess intrinsic bioreductive properties, i.e. they are reduced in hypoxia regions of mammalian systems to species (as yet unknown) which are then trapped—giving hypoxia selective radiopharmaceuticals. A further indication of the reducibility of certain technetium diaminedioxime complexes is the use of a non-specific chemical spot-test for a reducible moiety—the zinc/ammonia test. Example 19a demonstrates that, under such conditions, most of the technetium complexes studied, whether they contain a nitroimidazole or not, undergo reduction to a new species (as evidenced by HPLC). It is interesting to note that $^{99m}$Tc-Compound IV which has a PentAO ligand and hence a Tc(V) dioxo core appears inert to $Zn/NH_3$ and also exhibits very little hypoxia selectivity in the IPH screen. The radically different behaviour of $^{99m}$Tc-Compound I (BnAO) suggests that, contrary to literature conclusions[3], Tc-BnAO does not have a dioxo core and this is crucial to the bioreductive properties of the complex.

EP 544412 A2 (Example 8a) reports that $^{99}$Tc-PnAO (Compound X) is not reduced by the reductase enzyme xanthine oxidase (XOD). This invention demonstrates, however, that a number of $^{99m}$Tc-ligand complexes, including PnAO, are reduced by xanthine oxidase (see Example 19b). The different behaviour observed for $^{99m}$Tc-PnAO compared to the $^{99}$Tc complex is presumably due to the concentration of radiometal complex used in the assay.

The ligands of this invention can be synthesised according to Schemes 1 to 5 and Examples 1 to 17.

Scheme 1

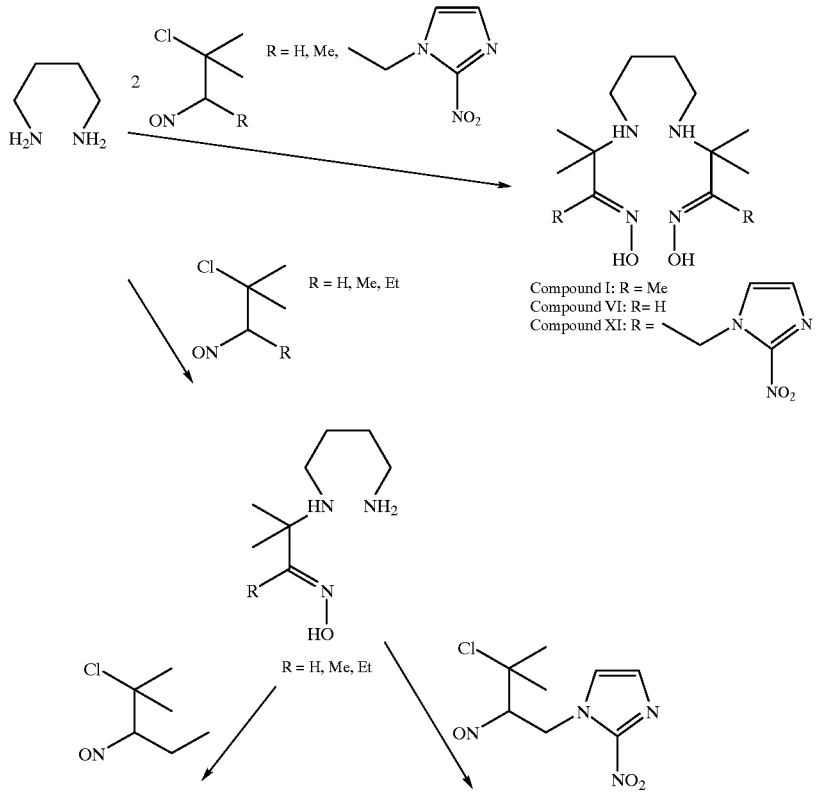

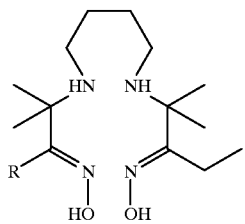
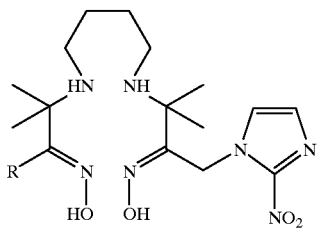
Compound VII: R = H
Compound VIII: R = Et
Compound IX: R = Me
Compound II: R = Me
Compound XII: R = H
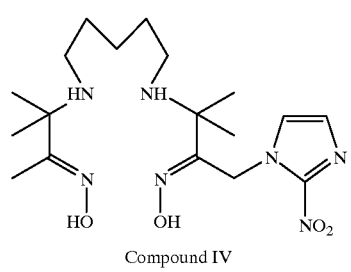
Compound IV
Scheme 2
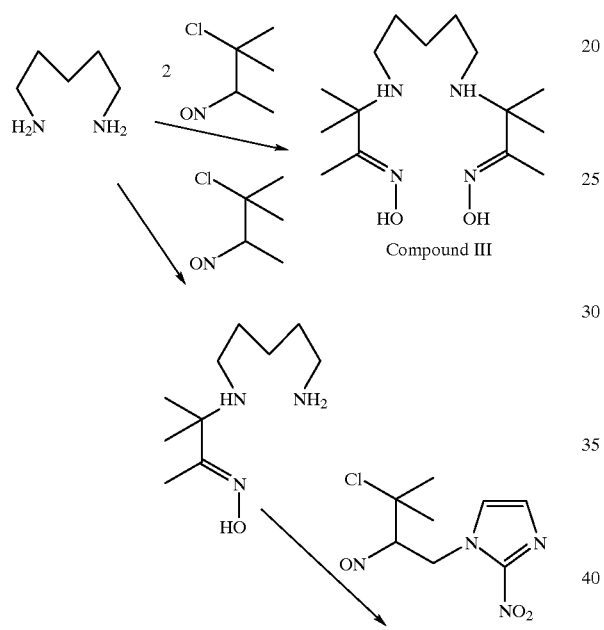
Scheme 3
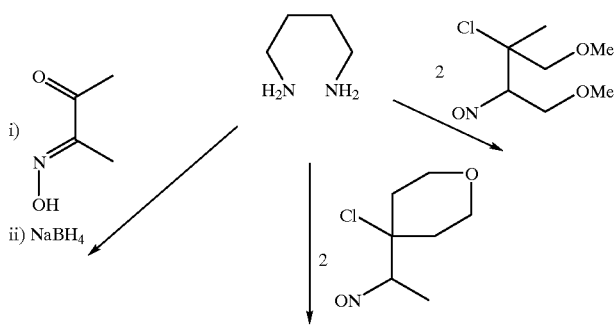

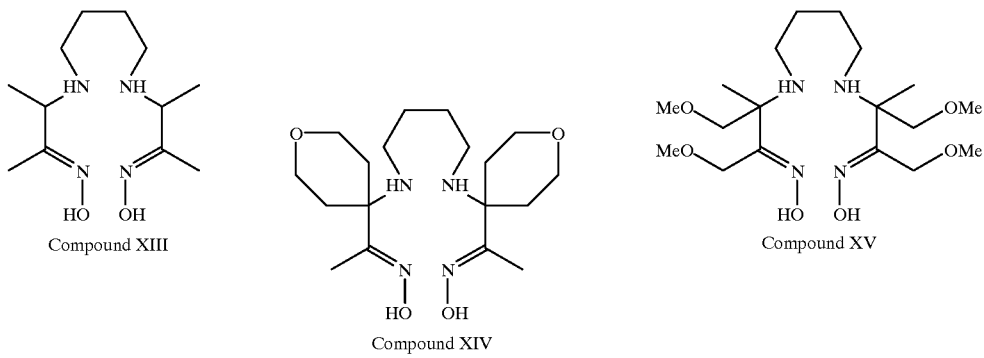

Compound XIII

Compound XIV

Compound XV

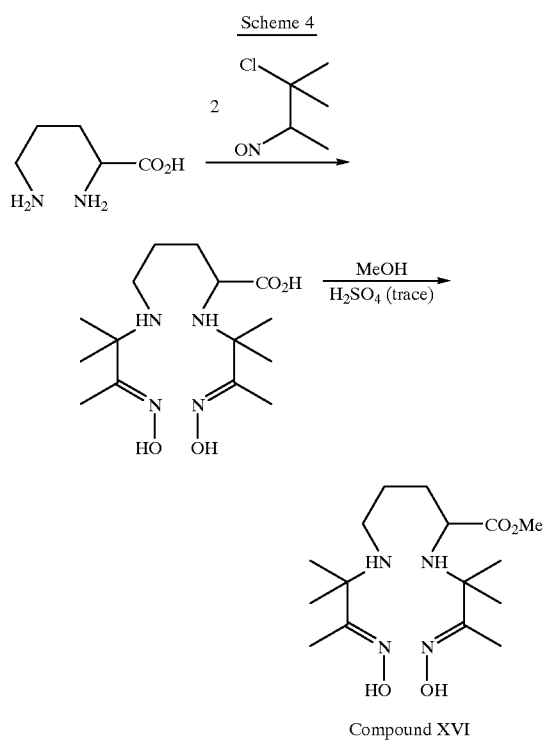

Scheme 4

Compound XVI

Scheme 5

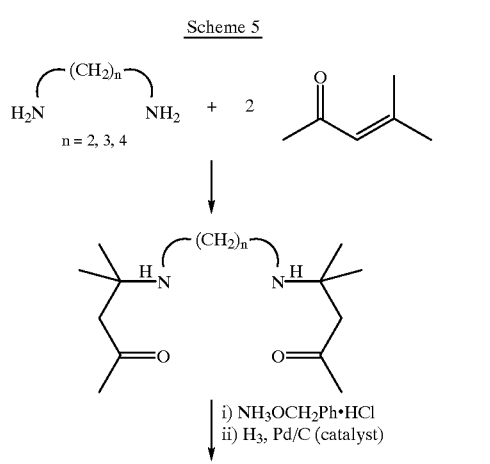

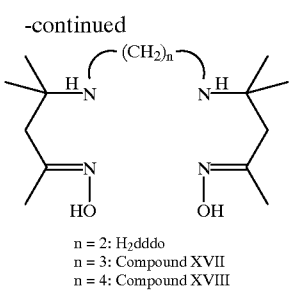

n = 2: H₂dddo
n = 3: Compound XVII
n = 4: Compound XVIII

EXPERIMENTAL

The synthesis of 2-(4-aminobutyl)amino-2-methyl-3-pentanone oxime is described herein. 3-(4-aminobutyl)amino-3-methyl-2-butanone oxime, 3-(5-aminopentyl)amino-3-methyl-2-butanone oxime and 2-(4-aminobutyl)amino-2-methyl-1-propanal oxime were prepared using analogous methods. H²dddO was prepared by the method of Schlemper et al.[10].

i) Synthesis of 2-(4-aminobutyl)amino-2-methyl-3-pentanone oxime

To a stirred solution of 1,4-diaminobutane (0.26 g; 2.9 mmol) and triethylamine (0.33 g; 3.2 mmol) in acetonitrile (5 ml) was added a solution of 2-chloro-2-methyl-3-nitrosopentane (0.485 g; 3.24 mmol) in acetonitrile (5 ml). After stirring for ca 10 minutes the product began to precipitate. The reaction mixture was stirred overnight and the product was filtered off and dried in vacuo to give a white powder, (0.5 g; 86%).

Analysis: m.p.: 125–128° C.; $^{13}$C NMR: (CDCl$_3$); δ (ppm): 11.2 (s), 19.3 (s), 24.2 (s), 26.4 (s), 26.8 (s), 40.4 (s), 43.7 (s), 61.5 (s), 161.6 (s).

ii) 3-(4-aminobutyl)amino-3-methyl-2-butanone oxime

Analysis: m.p.: 62–64° C.; $^1$H NMR: (D$_2$O); δ (ppm): 1.20 (s; 6H; —CH$_3$), 1.4–1.6 (m; 4H, —CH$_2$), 1.80 (s; 3H; —CH$_3$—C=N—O), 2.40 (t; 2H; CH$_2$—CH$_2$—N), 2.75 (t; 2H; CH$_2$—CH$_2$—N).

iii) 3-(5-aminopentyl)amino-3-methyl-2-butanone oxime

Analysis: m.p.: 174–176° C.; $^1$H NMR: (D$_2$O); δ (ppm): 1.20 (s; 6H; —CH$_3$), 1.3–1.6 (m; 6H, —CH$_2$), 1.75 (s; 3H; —CH$_3$—C=N—O), 2.35 (t; 4H; CH$_2$—CH$_2$—N).

iv) 2-(4-aminobutyl)amino-2-methyl-1-propanal oxime

Analysis: m.p.: 136–137° C.; $^1$H NMR: (D$_2$O); δ (ppm): 1.05 (s; 6H; —CH$_3$), 1.15 (m; 2H, —CH$_2$), 1.25 (m; 2H; —CH$_2$—), 2.20 (t; 2H; CH$_2$—CH$_2$—N), 2.45 (t; 2H; CH$_2$—CH$_2$—N), 7.15 (s; H—C=N).

Synthesis of 2-Chloro-2-methyl-3-nitrosopentane

Dry hydrogen chloride gas was passed into a mixture of 2-methyl-2-pentene (20 g, 237 mmol) and iso-amyl nitrite (55.67 g, 475 mmol) cooled to −20° C. The reaction mixture was left to stir at 0° C. overnight and the precipitated material was then filtered off and washed with cold (−20° C.) ethanol (3×5 ml). The product was dried in a stream of air and was used without further purification, (13 g, 36%).

Analysis: m.p.: 83–85° C.; $^{13}$C NMR: (CDCl$_3$); δ (ppm): 11.5 (s), 22.2 (s), 29.5 (s), 30.0 (s), 69.3 (s), 74.5 (s).

Synthesis of N-[3-chloro-2-(hydroxyamino)-3-methylbutyl]-2-nitroimidazole

2-Nitroimidazole (2 g, 17.7 mmol) was added to a solution of sodium hydroxide (0.76 g, 19 mmol) in water (20 ml). The solution was stirred for ca 1 h. at RT, the water was removed under reduced pressure and the residue dried in vacuo for at least ca 3 h.

To the sodium salt of 2-nitroimidazole prepared above was added acetonitrile (50 ml), 15-crown-5-ether (3.5 ml, 14.3 mmol) and 4-bromo-2-methyl-2-butene (2 ml; 17.4 mmol). The mixture was stirred at RT for ca 16 h. and then the solvent was removed to leave a crude semi-solid which was purified by column chromatography on silica. The intermediate product, 1-(3-methyl-2-butenyl)-2-nitroimidazole (80% yield) was eluted using a mixture of petroleum ether (40–60)/ethyl acetate (ratio 4:1 respectively).

The N-alkylated product of first step (1.0 g, 5.5 mmol) was dissolved in iso-amyl nitrite (1.0 ml, 7.4 mmol) at RT and then cooled in an ice bath (outside temp. measured −8° C.). Concentrated hydrochloric acid (0.9 ml, 36% HCl) was added dropwise while stirring. The reaction was stirred for ca 15 min. before storing overnight at −20° C.

Glacial acetic acid (10 ml) was added and the mixture was kept at −20° C. for ca 30–35 min. Methanol (10 ml, cold) was added and the reaction mixture was stored at −15° C. for ca 3 h., whence a white precipitate formed. The product was filtered very quickly, washed with ice-cold methanol (5 ml) and then dried in vacuo, yielding the compound as a white powder.

Analysis: m.p.=94–96° C. dec.; $^1$H NMR: (CD$_3$CN); δ (ppm): 1.80 (s; 6H; —CH$_3$), 5.43 (s; 2H; N=C—CH$_2$—N), 7.05 (s; 1H; $^4$H), 7.20 (s; 1H; $^5$H), 9.63 (s; 1H; N—OH). $^{13}$C NMR: (DMSO-d$_6$); δ (ppm): 30.02 (s), 42.38 (s), 70.66 (s), 126.41 (s), 127.53 (s), 153.25 (s).

Example 1

Synthesis of 4,9-diaza-3,3,10,10-tetramethyldodecan-2,11',-dione dioxime (Compound I, BnAO)

Into a 3 liter, 3 necked flask fitted with an Argon inlet, reflux condenser, overhead stirrer and pressure equalising dropping funnel was added acetonitrile (1000 ml), 1,4-diaminobutane (19.5 g, 0.23 mol) and sodium bicarbonate (37.2 g, 0.46 mol). This mixture was stirred vigorously at ambient temperature, under an argon atmosphere, to maintain a suspension of the insoluble bicarbonate. 2-chloro-2-methyl-3-nitrosobutane (60 g, 0.46 mol) was dissolved in acetonitrile (600 ml) and added dropwise, with stirring, into the reaction vessel over ca 15–20 minutes. Following the addition, the reaction mixture was stirred for a further 1 hour and then heated to ca 60° C. for 30 minutes. The reaction mixture was allowed to cool to RT and the white-solid present, (NaHCO$_3$/NaCl and product) was filtered off. The desired product was extracted into hot methanol, filtered hot, the solvent concentrated to ca 50% volume, cooled and refiltered. The solid material was dissolved in the minimum volume of hydrochloric acid (0.1M) and the pure product isolated, as a precipitate, by adjusting the pH of the solution to pH=11 using sodium hydroxide (0.1M).

After filtering and drying the product, recrystallisation from hot methanol, yielded 4,9-diaza-3,3,10,10-tetramethyldodecan-2,11-dione dioxime as white needles, (20 g; 30.4%).

Analysis: m.p.: 183–186° C.; $^1$H NMR: (DMSO-d$_6$); δ (ppm): 1.10 (s, 12H, —CH$_3$), 1.30 (m, 4H, —CH$_2$), 1.70 (s, 6H, —CH$_3$—C=N—O); 2.10 (m, 4H; —CH$_2$—N), 10.34 (s, 2H, Oxime). $^{13}$C NMR: (CD$_3$OD); δ (ppm): 10.3 (s), 26.4 (s), 29.7 (s), 45.0 (s), 59.4 (s), 162.2 (s).

Example 2

Synthesis of 3,3,10,10-tetramethyl-1-(2-nitro-1H-imidazo-1-yl-4,9-diazadodecan-2,11-dione dioxime (Compound II)

A solution of 1-(2-nitro-1-imidazola)-3-chloro-3-methylbutan-2-one-2-monoxime (656 mg; 2.66 mmol) in absolute ethanol (70 ml) was added to a slurry of 3-(4-aminobutyl)-amino-3-methyl-2-butanone oxime (500 mg; 2.66 mmol) and sodium bicarbonate (1 g; 11.97 mmol) in a mixture of dry acetonitrile (35 ml) and absolute ethanol (35 ml), over a period of ca 10'. The reaction mixture was stirred for ca 72 h., and then the solvent was removed under reduced pressure.

Water (30 ml) was added to the residual oil and the slurry was acidified to pH=4 using HCl (2M) yielding a clear solution. Any organic impurities were extracted into diethylether (3×50 ml) prior to the dropwise addition of NaOH (2M) to the aqueous phase. At pH=10–11, the product precipitated from solution and was isolated by filtration in air, washed with water, and dried in vacuo to yield Compound II as a cream powder.

Analysis: m.p.: 151–152° C.; $^1$H NMR: (CD$_3$OD); δ (ppm): 1.18 (s; 6H; —CH$_3$), 1.20 (s; 6H; —CH$_3$), 1.40 (m; 4H, —CH$_2$); 1.75 (s; 3H; —CH$_3$—C=N—O), 2.16 (t; 2H; CH$_2$—C̲H̲$_2$—N), 2.30 (t; 2H; —C̲H̲$_2$—CH$_2$), 5.28 (s; 2H; O—N=C—CH$_2$—N), 7.05 (s; 1H; $^4$H), 7.35 (s; 1H; $^5$H).

Example 3

Synthesis of 4,10-diaza-3,3,11,11-tetramethyltridecan-2,12-dione dioxime (Compound III, PentAO)

This compound was prepared according to the literature method[3].

Analysis: m.p.: 130–132° C.; $^1$H NMR: (CD$_3$OD); δ (ppm): 1.20 (s; 12H; —CH$_3$), 1.3–1.5 (m; 6H, —CH$_2$), 1.75 (s; 6H; —CH$_3$—C=N—O), 2.35 (t; 4H; CH$_2$—C̲H̲$_2$—N).

Example 4

Synthesis of 3,3,11,11-tetramethyl-1-(2-nitro-1H-imidazo-1-yl)-4,10-diazatridecan-2,12-dione dioxime (Compound IV)

This product was prepared by the method used for Compound II, substituting 3-(5-aminopentyl)amino-3-methyl-2-butanone oxime for 3-(4-aminobutyl)amino-3-methyl-2-butanone oxime.

Analysis: m.p.: 135–137° C.; $^1$H NMR: (CD$_3$OD); δ (ppm): 1.20 (s; 6H; —CH$_3$), 1.25 (s; 6H; —CH$_3$), 1.3–1.5 (m; 6H, —CH$_2$), 1.75 (s; 3H; —CH$_3$—C=N—O), 2.2–2.35 (m; 4H; CH$_2$—C̲H̲$_2$—N), 5.28 (s; 2H; O—N=C—C̲H̲$_2$—N), 7.05 (s; 1H; $^4$H), 7.35 (s; 1H; $^5$H).

Example 5

Synthesis of 3,3,9,9-Tetramethyl-1-(2-nitro-1H-imidazo-1-yl)-4,8-diazaundecane-2,10-dione dioxime (Compound V, Prior Art)

This compound was prepared by the method described in the Squibb Patent: EP 544412 A2, see Example 1, p.20–21.

Analysis: m.p.: 146–148° C.; $^1$H NMR: (CDCl$_3$); δ (ppm): 1.25 (s; 6H; —CH$_3$), 1.30 (s; 6H; —CH$_3$), 1.60 (s; 2H; —CH$_2$) 1.80 (s; 3H; —CH$_3$—C=N—O), 2.35 (q; 4H; CH$_2$—CH$_2$—N), 5.28 (s; 2H; O—N=C—CH$_2$—N), 7.05 (s; 1H; $^4$H), 7.35 (s; 1H; $^5$H).

Example 6

Synthesis of 3,8-diaza-2,2,9,9-tetramethyldecan-1,10-dial dioxime (Comround VI)

This compound was prepared in an analogous method to the published synthesis of PnAO$^9$, using 2-chloro-2-methyl-1-nitrosopropane.

Analysis: m.p.: 165–168° C.; $^1$H NMR: (CD$_3$OD); δ (ppm): 1.10 (s; 12H; —CH$_3$), 1.25 (m; 4H; —CH$_2$), 2.25 (t; 4H; CH$_2$—CH$_2$—N), 7.15 (s; 2H; H—C=N—O).

Example 7

Synthesis of 3,8-diaza-10-(hydroxyimino)-2,2,9,9-tetramethyl dodecanal oxime (Compound VII)

To a stirred solution of 2-(4-aminobutyl)amino-2-methylpropanal oxime (0.5 g; 2.9 mmol) in methanol (5 ml) was added a solution of 2-chloro-2-methyl-3-nitrosopentane (0.44 g; 2.9 mmol) in acetonitrile (5 ml). The reaction mixture was stirred overnight and the solid filtered off and recrystallised from methanol. The product, after drying in vacuo, gave colourless needles, (0.46 g; 58%).

Analysis: m.p.: 185–188° C.; $^1$H NMR: (CD$_3$OD); δ (ppm): 1.15 (t; 3H; CH$_2$—CH$_3$), 1.31 (s; 6H; —CH$_3$), 1.46 (s; 6H; —CH$_3$) 1.67 (m; 4H; —CH$_2$), 2.36 (q; 2H; =CH$_2$—CH$_3$), 2.63 (t; 2H; CH$_2$—N), 2.84 (t; 2H; CH$_2$—N), 7.31 (s; 1H; H—C=N—O). $^{13}$C NMR: (CD$_3$OD); δ (ppm): 11.1 (s), 19.4 (s), 23.7 (s), 24.9 (s), 26.7 (s), 27.8 (s), 43.6 (s), 43.7 (s), 56.5 (s), 62.1 (s), 154.5 (s), 160.9 (s).

Example 8

The Synthesis of 5,10-diaza-4,4,11,11-tetramethyltetradecan-3,12-dione dioxime (Compound VIII)

To a stirred solution of 2-(4-aminobutyl)amino-2-methyl-3-pentanone oxime (0.2 g; 1 mmol) and triethylamine (0.11 g; 1 mmol) in methanol (5 ml) was added a solution of 2-chloro-2-methyl-3-nitrosopentane (0.116 g; 1.08 mmol) in acetonitrile (5 ml). The reaction mixture was stirred overnight and the solvent removed in vacuo to yield the crude product. This material was dissolved in methanol and the product precipitated by the addition of diethylether. After filtering, the product was dried in vacuo to give a white powder (0.18 g; 58%).

Analysis: m.p.: 194–197° C.; $^1$H NMR: (CD$_3$OD); δ (ppm): 1.14 (t; 6H; CH$_2$—CH$_3$), 1.39 (s; 12H; —CH$_3$), 1.65 (m; 4; —CH$_2$) 2.34 (q; 4H; =CH$_2$—CH$_3$), 2.71 (m; 4H; CH$_2$—N). $^{13}$C NMR: (CD$_3$OD); δ (ppm): 11.12(s), 19.2 (s), 24.3 (s), 27.1 (s), 43.7 (s), 61.1 (s), 162.1(s).

Example 9

The Synthesis of 4,9-diaza-3,3,10,10-tetramethyltridecan-2,11-dione dioxime (Compound IX)

To a stirred solution of 3-(4-aminobutyl)amino-3-methyl-2-butanone oxime (0.5 g; 2.67 mmol) and triethylamine (0.3 g; 2.9 mmol) in methanol (5 ml) was added a solution of 2-chloro-2-methyl-3-nitrosopentane (0.43 g; 2.9 mmol) in acetonitrile (5 ml). The reaction mixture was stirred overnight and the solvent removed in vacuo to yield the crude product. This material was dissolved in methanol and the product precipitated by the addition of diethylether. After filtering, the product was dried in vacuo to give a white powder (0.46 g; 57%).

Analysis: m.p.: 190–193° C.; $^1$H NMR: (CD$_3$OD); δ (ppm): 1.15 (t; 3H; CH$_2$—CH$_3$), 1.37 (s; 6H; —CH$_3$), 1.42 (s; 6H; —CH$_3$); 1.67 (m; 4H; —CH$_2$), 1.86 (s; 3H; —CH$_3$), 2.35 (q; 2H; =CH$_2$—CH$_3$), 2.68 (t; 2H; CH$_2$—N), 2.77 (t; 2H; CH$_2$—N). $^{13}$C NMR: (CD$_3$OD) δ (ppm): 9.7 (s), 11.2 (s), 19.3 (s), 24.4 (s), 26.9 (d), 43.7 (d), 60.8 (s), 61.6 (s), 158.5 (s), 161.6 (s).

Example 10

The Synthesis of 1,12-bis(2-Nitro-1-imidazolyl)-4,9-diaza-3,3,10,10-tetramethyldodecan-2,11-dione dioxime (Compound XI)

To a stirred solution of 1,4-diaminobutane (90 mg, 1 mmol) and triethylamine (200 mg, 2 mmol) in methanol (10 cm$^3$) was added dropwise a solution of 1-(3-chloro-3-methyl-2-nitroso)butyl-2-nitroimidazole (500 mg, 2 mmol) in acetonitrile (10 cm$^3$). The reaction mixture was stirred for 48 h, after which time the reaction mixture was filterd.

The solid material was found to be 1,12-bis(2-Nitro-1-imidazolyl)-4,9-diaza-3,3,10,10-tetramethyldodecan-2,11-dione dioxime, (165 mg, 35%)

Analysis: m.p.: 168–170° C.; $^1$H NMR: (d$_6$-DMSO); δ (ppm): 1.18 (14H,s, Overlapping resonances), 2.08 (4H,s), 2.50 ($^2$H,t,J$_{HH}$ 7.2 Hz), 5.23(4H,s), 7.11(1H, d,J$_{HH}$ 1.2 Hz), 7.29H, d,J$_{HH}$ 1.2 Hz). $^{13}$C NMR: (CD$_3$OD); δ (ppm): 25.48(×4)(CH$_3$), 27.96(CH$_2$), 42.39(×2)(CH$_2$), 56.86(×2) (q), 126.48 (×2)(CH), 127.35 (×2)(CH), 145.35(×2)(q), 156.53(×2)(q).

Example 11

The Synthesis of 3,8-diaza-10-hydroxyimino-11-(2-nitro-1-imidazolyl)-2,2,9,9-tetramethylundecanal oxime (Compound XII)

To a stirred solution of 2-(4-aminobutyl)amino-2-methylpropanal oxime (191 mg, 1.1 mmol) and triethylamine (121 mg, 1.21 mmol) in methanol (10 cm$^3$) was added a solution of 1-(3-chloro-3-methyl-2-nitroso)butyl-2-nitroimidazole (300 mg, 1.21 mmol) in acetonitrile (10 cm$^3$). The reaction mixture was stirred overnight, and volatile components then removed in vacuo to leave a yellow semi-solid material. This product was then taken up in water (10 cm$^3$) and any insoluble material filtered off. The filtrate was purified using reverse phase HPLC eluting with 50:50 methanol/water to give Compound XII as a yellow viscous oil. (40 mg, 10%).

Analysis: $^1$H NMR: (CD$_3$OD); δ (ppm): 1.17–2.4 (4H,m, Overlapping resonances), 1.26 (6H,s), 1.27 (6H,s) 2.26 (2H, t,J$_{HH}$ 7.2 Hz), 2.50 (2H, t,J$_{HH}$7.2 Hz), 5.35(2H,s,), 7.09(1H, d,J$_{HH}$ 1.2 Hz), 7.27 (1H,s), 7.34(1H,d,J$_{HH}$ 1.2 Hz). $^{13}$C NMR: (CD$_3$OD); δ (ppm): 25.14(×2)(CH$_3$), 25.8 (×2)(CH$_3$), 28.45 (CH$_2$), 28.98 (CH$_2$), 41.99 (CH$_2$), 43.87 (CH$_2$), 43.91 (CH$_2$), 55.82 (q), 58.52 (q) 127.58 (CH), 128.17 (CH), 155.15 (q).

Example 12

The Synthesis of 4,9-Diaza-3,10-dimethyldodecan-2,11-dione dioxime (Compound XIII)

A 4,9-Diaza-3,9-diene-3,10-dimethyldodecan-2,11-dione dioxime

Butan-2,3-dione monooxime (10.11 g 0.1 mol) was dissolved in benzene (125 cm$^3$) and heated under reflux.

A solution of 1,4-diaminobutane (3.97 g, 45 mmol) in benzene (100 cm$^3$) was added dropwise over a period of five hours, heating was continued over night. On cooling, a cream solid precipitated which was isolated by vacuum filtration and used without further purification (10.8 g, 94%).

Analysis: $^1$H NMR: DMSO; δ (ppm): 1.5 (4H, brs, CH$_2$), 1.72 (6H, s, CH$_3$), 1.80 (6H,s, CH$_3$), 3.20 (4H, brs, NCH$_2$). $^{13}$C NMR: DMSO; δ (ppm): 9.12 (×2), CH$_3$, 13.1 (×2)CH$_3$, 28.7 (×2)CH$_2$, 51.2 (×2)(NCH$_2$), 156.7 (×2)q, 163.6 (×2)q.

B 4,9-Diaza-3,10-dimethyldodecan-2,11-dione dioxime

Sodium borohydride (0.3 g, 7.85 mmmol) was added dropwise to a stirred, precooled (ice.salt) solution of the diimine prepared above (2 g, 7.85 mmol) in absolute ethanol (20 cm$^3$) over a period of 30 minutes. The reaction mixture was stirred for a further 2 hours, water (10 cm$^3$) was then added and the pH of the aqueous phase made neutral by the addition of dilute HCl. The solvent was removed in vacuo to give a white powder.

A sample of this material was purified using reverse phase HPLC using water/methanol (50:50) as the eluent to give a colourless solid.

Analysis: m.p.: 210° C. (decomposes); Elemental Analysis, for C$_{12}$H$_{26}$N$_4$O$_2$. Expected: C 55.79, H 10.14, N 21.69. Found: C 55.72, H 10.44, N 21.18%; $^1$H NMR: D$_2$O; δ (ppm): 1.49 (6H, d, 6.8 Hz, CH$_3$), 1.76–1.85 (4H, m, CH$_2$), 1.91(6H, s, CH$_3$), 3.0–3.06 (4H, m, NCH$_2$), 3.92 (2H, q, 6.8 Hz,NCH); $^{13}$C NMR: CD$_3$OD; δ (ppm): 11.6 (×2)(CH$_3$), 16.4 (×2)(CH$_3$), 24.5 (×2)(CH$_2$), 58.4 (×2)(CH), 153.2(×2) (q).

Example 13

The Synthesis of N,N'-Bis(4-acetyl-tetrahydroryran-4-yl)-1,4-diaminobutane dioxime (Compound XIV)

A solution of 4-chloro-4-(1-nitrosoethyl)tetrahydropyran (500 mg, 2.91 mmol) in acetonitrile (15 cm$^3$) was added to a stirred solution of 1,4-diaminobutane (120 mg, 1.36 mmol) and triethylamine (300 mg, 2.98 mmol). On addition a white solid precipitated from the reaction mixture. The reaction was left to stir for a further 15 minutes after which time the solid material was filtered off under vacuum. Recrystallisation from methanol gave the product as a white powder (150 mg, 30%)

Analysis: m.p.: 183° C.; $^1$H NMR: CDCl$_3$/CD$_3$OD); δ (ppm): 1.45 (4H, m, CH$_2$), 1.65 (4H,m with doublet of triplet character, CH), 1.79 (3H, s, CH$_3$), 1.80 (3H, s, CH$_3$), 2.03 (4H, m with doublet character, CH), 2.33(4H, m,CH$_2$), 3.60 (4H, m with doublet of triplet character, CH), 3.20 (4H, m, CH). $^{13}$C NMR: CDCl$_3$/CD$_3$OD); δ (ppm): 9.17 (×2)(CH$_3$), 28.69 (×2)(CH$_2$), 34.42 (×2)(CH$_2$), 42.18(×2)(CH$_2$), 57.86 (×2)(q), 64.79 (×2)(CH$_2$), 158.65(×2)(q)

Example 14

Synthesis of 3,10-Bis(methoxymethyl)-4,9-diaza-1,12-dimethoxy-3,10-dimethyldodecan-2,11-dione dioxime (Compound XV)

A solution of 2-chloro-2-methoxymethyl-4-methoxy-3-nitrosobutane (0.19 g, 1.2 mmol) in acetonitrile (2.5 ml) was added to a stirred suspension of 1,4-diaminobutane (44 mg, 0.6 mmol) and sodium bicarbonate (0.25 g) in acetonitrile (2.5 ml). Following the addition, the reaction mixture was heated under reflux for ca 5 h. and stirred at RT for a further ca 72 h.

After removing the solvent in vacuo, water (30 ml) was added to the residual oil and the slurry was acidified to pH=4 using HCl (2M) yielding a clear solution. Any organic impurities were extracted into diethylether, (3×50 ml) prior to the dropwise addition of NaOH (2M) to the aqueous phase. At pH=10–11, the product was extracted into dichloromethane (3×50 ml). The dichloromethane fractions were bulked together, dried over magnesium sulphate, filtered and taken to dryness to yield a colourless semi-solid.

A sample of this material was purified by reverse phase HPLC using the following conditions:
 Column: PRP 1
 Solvent A: H$_2$O
 Solvent B: MeCN
 Flow: 2.5 ml/min
 Gradient: 0–100% Solvent B over 15 minutes.
 Detector: U.V; wavelength set at 210 nm.
 Retention Time: 13.5 minutes.
 Analysis; $^1$H NMR: CDCl$_3$ (Isomers present); δ (ppm): 1.25 (6H, s, CH$_3$), 1.50 (4H, br, CH$_2$), 2.40 (4H, br, CH$_2$—N), 3.30 (12H, m, overlapping O—CH$_3$ resonances), 3.45 (4H, m (masked), —CH$_2$—OMe), 4.3 (4H, m, N=C—CH$_2$—OMe).

Example 15

The Synthesis of 4,9-diaza-3,3,10,10-tetramethyldodecan-2,11-dione dioxime-8-carboxylic acid methyl ester (Compound XVI)

To a freshly prepared solution of sodium ethoxide, (294 mg Na in 20 ml of dry ethanol), stirred under a dry dinitrogen atmosphere, was added L-ornithine.HCl, (1 g, 6 mmol). The reaction mixture was stirred for ca 1 h at RT and then the solvent was removed in vacuo. The free base generated from this reaction was immediately redissolved in a mixture of dry acetonitrile (10 ml) and dry ethanol (15 ml) and stirred. A slurry of 2-chloro-2-methyl-3-nitrosobutane (1.58 g, 12 mmol) and sodium bicarbonate (4.5 Meq) in dry acetonitrile was added dropwise to the free base L-ornithine solution over a period of 10 minutes, and the reaction mixture was stirred at RT for ca 18 h.

After the solvent was removed in vacuo, water (40 ml) was added to the residue. The resulting slurry was acidified to pH=4 using HCl (2M) yielding a clear solution. Any organic impurities were extracted into diethylether (3×50 ml). The aqueous phase was adjusted to pH=11 and then taken to dryness. The residue was redissolved in dry methanol (20 ml) and 4 drops of H$_2$SO$_4$ (conc) was added. The solution was heated under reflux for ca 4 h. and stirring continued at RT for a further 18 h.

Removal of solvent in vacuo, gave a gummy residue which was purified by reverse phase HPLC (see below), yielding a clear oil of 4,9-diaza-3,3,10,10-tetramethyldodecan-2,11-dione dioxime-8-carboxylic acid methyl ester, (150 mg).

HPLC System:
 Column PRP-1
 Solvent A: H$_2$O
 Solvent B: MeCN
 Flow Rate: 2.5 ml/min
 Detection: U.V.; wavelength set at 210 nm
 Gradient 0%–100% Solvent B over 20'
 Retention Time of Product: 4.5 minutes
 Analysis: $^1$H NMR: CD$_3$OD; δ (ppm): 1.50 (s, 12H, —CH$_3$), 1.95 (m, 4H, CH$_2$ and s, 6H, CH$_3$—C=N—O); 3.00 (t, 2H, —CH$_2$—N), 3.60 (t, 1H, N—CH), 3.70 (s, O—CH$_3$).

Example 16

Synthesis of 5,9-Diaza-4,4,10,10-tetramethyltridecan-2,12-dione dioxime (Compound XVII)

A 5,9-diaza-4,4,10,10-tetramethyltridecan-2,12-dione di(O-benzyloxime),2HCl

4-Methylpent-3-en-2-one (2 g; 20.4 mmol) was added with stirring to 1,3-diaminopropane (0.74 g, 10 mmol). The progress of the reaction was monitored by $^{13}$C NMR and after a period of 20 minutes, the reaction was judged to be complete. Methanol (10 ml) and O-benzylhydroxylamine hydrochloride (3.25 g, 20.4 mmol) were added to the reaction mixture. The reaction was stirred for ca 1 h. after which time the solvent was removed in vacuo to give a yellow viscous material. Water (20 ml) was added and the product was extracted into dichloromethane. The dichloromethane was removed in vacuo to give the crude product as a honeycomb solid. Recrystallisation from water/methanol (95:5%) gave the product as colourless plates, (3.2 g, 65%).

Analysis; m.p.: 163–165° C.; Elemental Analysis, for $C_{29}H_{44}N_4O_2.2HCl.2H_2O$; Expected: C 59.07, H 8.55, N 9.50. Found: C 59.36, H 8.55, N 9.98%; $^1$H NMR: CDCl$_3$/TMS; δ (ppm): 1.38 (12H, s, CH$_3$), 1.94 (6H, s, CH$_3$), 2.15 (2H, m, CH$_2$), 2.57 (4H, s, CH$_2$), 2.91 (4H, m, NCH$_2$), 5.08 (4H, s, OCH$_2$), 7.31 (10H brs). $^{13}$C NMR: CD$_3$OD; δ (ppm): 17.32 (×2)(CH$_3$), 24.23 (×4)(CH$_3$), 25.02 (CH$_2$), 39.76 (×2)(CH$_2$), 42.84 (×2)(CH$_2$), 60.48 (×2)(q), 76.64 (×2)(CH$_2$), 128.93 (×2)(CH), 128.93 (×2)(CH), 128.98 (×4)(CH), 129.51 (×4)(CH), 139.17 (×2)(q) 156.72 (×2)(q).

B 5.9-Diaza-4,4,10,10-tetramethyltridecan-2,12-dione dioxime

To a stirred solution of the O-benzyl protected material prepared above (200 mg) in a mixture of methanol (15 ml) and formic acid (5 ml), under a dry dinitrogen atmosphere, was added a 10% palladium on carbon catalyst (20 mg). This mixture was hydrogenated at atmospheric pressure until the reaction was complete (ca 1 h.). The reaction mixture was filtered through a glass frit (porosity 4) and celite, and the solvent and other volatile components then removed in vacuo, yielding the product as a glassy semi-solid in essentially quantitative yield. To ensure a completely pure product, a small quantity of this material was dissolved in water and treated with sodium hydrogen carbonate prior to performing reverse phase HPLC using water/methanol (50:50%) as the eluent. The product was isolated as a viscous liquid.

Analysis; $^1$H NMR: D$_2$/DSS δ (ppm): 1.42 (12H, s, CH$_3$), 1.94 (6H, s, CH$_3$), 2.12 (2H, m, CH$_2$), 2.67 (4H, s, CH$_2$), 3.14 (4H, m, NCH$_2$). $^{13}$C NMR: CD$_3$OD; δ (ppm): 16.16 (×2)(CH$_3$), 24.71 (×4)(CH$_3$), 24.94 (CH$_2$), 39.67 (×2)(CH$_2$), 42.31 (×2)(CH$_2$), 59.96 (×2)(q), 155.75 (×2)(q).

Example 17

Synthesis of 5,10-Diaza-4,4,11,11-tetramethyltetradecan-2,13-dione dioxime (Compound XVIII)

A 5,10-Diaza-4,4,11,11-tetramethyltetradecan-2,13-dione di(O-benzyloxime),2HCl

This material was prepared as described previously for Compound XVII from 4-methylpent-3-en-2-one, (2 g, 20 mmol), 1,4-diaminobutane (0.9 g, 10 mmol) and O-benzylhydroxylamine hydrochloride (3.18 g, 20 mmol) in methanol (25 ml). After the addition of the O-benzylhydroxylamine hydrochloride the reaction was stirred overnight. Methanol was removed in vacuo to give a yellow viscous oil. Water (20 ml) and dichloromethane (20 ml) were added to the residue and the mixture was shaken vigorously. On standing the product crystallised at the interface of the liquids as colourless needles, (2.6 g, 47%).

Analysis; m.p.: 157–160° C.; Elemental Analysis, for $C_{30}H_{46}N_4O_2.2HCl.2H_2O$; Expected: C 59.69, H 8.68, N 9.28. Found: C 59.66, H 9.09, N 9.58%; $^1$H NMR: CDCl$_3$/TMS; δ (ppm): 1.43 (12H, s, CH$_3$), 1.84 (4H, CH$_2$), 1.94 (6H, s, CH$_3$), 2.67 (4H, s, CH$_2$), 2.89 (4H, m, NCH$_2$), 5.08 (4H, s, OCH$_2$), 7.32 (10H m). $^{13}$C NMR: CDCl$_3$/TMS; δ (ppm): 17.22 (×2)(CH$_3$), 23.56 (×4)(CH$_3$), 23.82 (×2)(CH$_2$), 40.54 (×2)(CH$_2$), 42.96 (×2)(CH$_2$), 59.90 (×2)(q), 75.79 (×2)(CH$_2$), 127.90 (×5)(CH), 128.56 (×4)(CH), 138.12 (×2)(q), 154.48 (×2)(q).

B 5,10-Diaza-4,4,11,11-tetramethyltetradecan-2,13-dione dioxime

To a stirred solution of the O-benzyl protected material prepared above (200 mg) in a mixture of methanol (15 ml) and formic acid (5 ml), under a dry dinitrogen atmosphere, was added a 10% palladium on carbon catalyst (20 mg). This mixture was hydrogenated at atmospheric pressure until the reaction was complete (ca 1 h.). The reaction mixture was filtered through a glass frit (porosity 4) and celite, and the solvent and other volatile components then removed in vacuo, yielding the product as a colourless semi-solid in essentially quantitative yield.

Analysis; $^1$H NMR: D$_2$O/DSS; δ (ppm): 1.41 (12H, s, CH$_3$), 1.76 (4H, br, CH$_2$), 1.93 (6H, s, CH$_3$), 2.67 (4H, s, CH$_2$), 3.07 (4H, m, NCH$_2$). $^{13}$C NMR: D$_2$O/DSS; δ (ppm): 18.20 (×2)(CH$_3$), 25.96 (×2)(CH$_2$), 26.04 (×4)(CH$_3$), 43.02 (×2)(CH$_2$), 43.85 (×2)(CH$_2$), 61.36 (×2)(q), 159.54 (×2)(q).

Example 18

Preparation of $^{99m}$Tc Complexes

The following general method was used to prepare the $^{99m}$Tc complexes of the ligands given in Examples I, II, VI to IX and XII to XV.

Ligand (1 mg) was dissolved in a mixture of 0.1M HCl (0.1 ml) and distilled water (0.9ml) in a sealed vial. The pH of the ligand solution was adjusted to pH=8 using 0.1M NaOH, and 0.25 GBq $^{99m}$TcO$_4^-$, (1 ml generator eluate), stannous tartrate, (0.3 ml of a 0.1 mg/ml solution in water) and 0.9% aq. NaCl (3 ml) was added. After standing at room temperature for ca. 30' the RCP of the $^{99m}$Tc complex was assessed by TLC and HPLC:

| Technetium Complex of | $^{99m}$Tc Complex (%) | HPLC (t$_R$ minutes) |
|---|---|---|
| Compound I | >95 | 4.0 |
| Compound II | >95 | 4.9 |
| Compound VI | >95 | 3.8 |
| Compound VII | >95 | 3.8 |
| Compound VIII | >95 | 4.8 |
| Compound IX | >95 | 3.9 |
| Compound XII | >95 | 4.4 |
| Compound XIII | >95 | 4.7 |
| Compound XIV | 73 | 6.8 |
| Compound XV | >95 | 3.4/3.7* |
| Compound XVI | >95 | 3.6 |

* = two $^{99m}$Tc-labelled isomers observed by HPLC

Preparation of $^{99m}$Tc Complex of Compounds III, IV, XI, H$_2$dddo, XVII, and XVIII Ligand (0.25 mg) was dissolved in a mixture of 0.1M HCl (0.1 ml) and distilled water (0.9 ml) in a sealed vial. The pH of the ligand solution was adjusted to pH=8 using 0.1M NaOH, and 0.25 GBq $^{99}Tc_4$-, (1 ml generator eluate), stannous tartrate, (0.3 ml of a 0.1 mg/ml solution in water) and 0.9% aq. NaCl (3 ml) was added. After standing at room temperature for ca. 30' the RCP of the $^{99m}Tc$ complex was assessed by TLC and HPLC:

| Technetium Complex of | $^{99m}Tc$ Complex (%) | HPLC ($t_R$ minutes) |
|---|---|---|
| Compound III | >90 | 4.0 |
| Compound IV | >90 | 5.3 |
| H$_2$dddo | >95 | 3.8 |
| Compound XI | >95 | 6.4 |
| Compound XVII | >95 | 4.1 |
| Compound XVIII | 62 | 3.4 |

Preparation of $^{99m}Tc$ Complex of Compound V

Ligand (0.2 mg) was dissolved in methanol (50 microlitres) in a sealed vial, and 0.25 GBq $^{99m}TcO_4$-, (1 ml generator eluate), stannous tartrate, (1 ml of a 0.1 mg/ml solution in water) and 0.9% aq. NaCl (4 ml) was added to the mixture. After standing at room temperature for ca. 30', >95% $^{99m}Tc$ complex was formed as judged by TLC and HPLC ($t_R$=9.3').

Analytical Methods:

Thin Layer Chromatography:

Whatman No. 1 paper eluted with 50% aqueous acetonitrile. Reduced hydrolysed Tc=$R_f$ 0.0.

ITLC SG eluted with 0.9% aq. NaCl Free pertechnetate= $R_f$ 1.0.

% $^{99m}Tc$ Complex=100—free pertechnetate—reduced hydrolysed Tc.

HPLC:

Hamilton PRP-1 column, eluted at 2 ml/min. Gradient System:

100% pH=5.6 50 mM sodium acetate to 100% tetrahydrofuran over 17 minutes.

Example 19 a) Zinc in Ammonium Chloride Solution Reduction Test

Zinc powder (20 mg) was weighed into a glass vial. The vial was capped, oversealed and purged with nitrogen gas. Nitrogen purged (2 mg/ml] ammonium chloride solution (1 ml) was added to the vial containing the zinc powder.

1 ml of the $^{99m}Tc$-complex preparation was then added to the reducing mixture, shaken and left standing for 15 minutes. The mixture was then filtered into a N$_2$ filled vial through an 0.22 µm Acrodisc filter. The filtrate was then assayed by HPLC.

Using this method a positive result was indicated by changes in the HPLC behavior of the complex. In practice this usually involved the loss of the original $^{99m}Tc$-complex HPLC peak and the appearance of another new peak or peaks in the HPLC. No change in the HPLC profile of a $^{99m}Tc$-complex was noted as a negative result.

The $^{99m}Tc$-complexes of the following ligands gave positive test results: Compounds I, II, and IV–X.

The $^{99m}Tc$-complexes of the following ligands gave negative test results: Compound III, PentAO.

b) Xanthine Oxidase (XOD) with Hypoxanthine in Phosphate Buffered Saline (PBS)

Xanthine oxidase (16 mg) was weighed into a P6 vial. the vial was capped, oversealed and purged with nitrogen gas. Nitrogen purged phosphate buffered saline (1 ml) was added to the vial containing the xanthine oxidase.

Hypoxanthine (4.1 mg) was weighed into a P6 vial. The vial was capped, oversealed and purged with nitrogen gas. To the hypoxanthine was added (1 ml) of the xanthine oxidase in PBS.

1 ml of the ligand solution or 1 ml of the $^{99m}Tc$-complex preparation was then added to the reducing mixture, shaken, and aliquots were taken at 20 minute time intervals.

These were assayed by HPLC as given in Example 11a (above).

The $^{99m}Tc$-complexes of the following ligands gave positive test results: Compounds I, II, IV, V and X.

Example 20

Biodistribution in Rats—Methods

The quantitative biodistribution was studied in male rats at 2 minutes, 1 hour and 4 hours post-injection Rats under light anaesthesia were injected intravenously with 0.1 ml of test agent. Three rats were sacrificed (anaesthesia followed by exsanguination) at 2, 60 and 240 minutes, post-injection. The percentage of the injected dose in the excreta and organs and tissues was determined by dissection and assay for radioactivity in an automatic gamma counter. Table 2 shows the data for the complexes studied with figures expressed as percent injected dose.

Example 21

Isolated Perfused Heart

In the experimental model isolated (Langendorff) rat hearts are perfused, following an initial equilibration period, with either oxic gassed (95% O$_2$, 5% CO$_2$) or hypoxic gassed (95% N$_2$, 5% CO$_2$) modified Kreb's-Henseleit buffer at constant flow. For both studies a mixture of test agent ($^{99m}Tc$ complex or $^{123}I$-IAZA), $^3H$-misonidazole and $^{14}C$-DTPA are slowly infused into the perfusate for a 20 minute period. A 15-minute cold buffer washout period follows. y activity in the heart is monitored using a collimated NaI probe detector positioned over the heart.

Samples of active perfusate and hearts are assayed for y counts and, following suitable processing using standard techniques, β-counts.

Activity in hearts, relative to perfusate activity, is calculated for each nuclide and data evaluated for each compound for activity in hypoxic and oxic hearts (hypoxic:oxic ratio) and also relative to the $_3$H-misonidazole activity (normalised retention) using Formula 1.

Formula 1: Normalised retention =

$$\frac{\text{activity in heart (test)}}{\text{total infused activity (test)}} \bigg/ \frac{\text{activity in heart }(^3H\text{–miso})}{\text{total infused activity }(^3H\text{–miso})}$$

Results

Table 1 gives the results. Typical graphical probe output data for $^{99m}Tc$ complexes of Compound I, Compound IV and PnAO are appended.

| $^{99m}$Tc complex of | Hypoxic/Oxic Ratio (H/O) | Normalised Hypoxic Retention |
|---|---|---|
| Compound I, BnAO | 54 | 2.2 |
| Compound II | 28 | 5.1 |
| Compound IV | 2.4 | 0.49 |
| Compound V (Prior Art) | 10 | 8.4 |
| PnAO | 5.1 | 0.50 |
| Compound VI | 3.2 | 0.67 |
| Compound VII | 8.8 | 1.5 |
| Compound VIII | 34 | 2.2 |
| Compound IX | 8.4 | 2.1 |
| H$_2$dddo | 1.8 | 0.49 |
| Compound XI | 3.4 | 0.98 |
| Compound XII | 9.5 | 1.9 |
| Compound XV | 1.2 | 1.4 |
| Compound XVI | 4.0 | 0.22 |
| $^{123}$I-IAZA | 10 | 2.7 |

Example 22

A formulated freeze dried kit has been prepared which contains a lyophilised mixture of 0.20 mg of Compound I, 0.04 mg of methylene diphosphonic acid, 0.02 mg of stannous chloride dihydrate, 2.8 mg of sodium hydrogen carbonate and 4.9 mg of sodium chloride. When a kit of this composition is reconstituted with $^{99m}$Tc-pertechnetate generator eluate in sterile saline (0.9% w/v), the $^{99m}$Tc-complex of Compound I is formed in ≧298% radiochemical purity after a reaction time of fifteen minutes at room temperature.

CONCLUSION

In the isolated buffer perfused rat heart model described the H/O ratio of the $^{99m}$Tc complexes of compounds I and II are significantly greater than seen for other $^{99m}$Tc test agents and $^{123}$I-IAZA. In addition the normalised hypoxic retention for both compounds is an intermediate value being greater than that for $^{99m}$Tc-PnAO and being at least 2 times greater than $^3$H misonidazole itself in the model and at least equivalent to $^{123}$I-IAZA (a radioiodine compound known to image hypoxia).

REFERENCES

1) W A Volkert et al., Int.J.Nucl.Med.Biol., 11, 243 (1984).
2) F Budsky et al., Nukleon, (1), 14 (1990). CA 113 187327d.
3) S Jurisson et al. Inorg.Chem., 26 3576 (1987).
4) D E Troutner et al., Acta.Cryst.Sect.C., C40, 1544 (1984).
5) D E Troutner et al. Paper INOR 129, ACS 192nd Meeting, Sep. 7–12, (1986).
6) D Groshar et al., J.Nucl.Med. 34, 885 (1993).
7) R B Moore et al. ibid, 34, 405 (1993).
8) W J Koh et al. ibid, 34 Supplement P252 (1989).
9) E G Vassian et al., Inorg.Chem., 6, 2043 (1967).
10) E O Schlemper et al. J.Coord.Chem., 16, 347 (1988).

TABLE 2

Rat Biodistribution

| Compound | Structure | RCP | Time | Muscle | Blood | Kidney | Bladder/Urine | Liver | Gut |
|---|---|---|---|---|---|---|---|---|---|
| I | 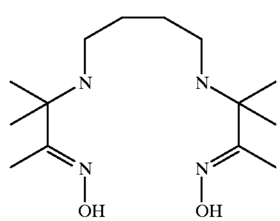 | 100 | 2 | 35.2 | 9.7 | 7.5 | 0.6 | 10.6 | 11.2 |
| | | | 60 | 12.5 | 2.4 | 5.6 | 38.9 | 9.1 | 22.3 |
| | | | 240 | 3.5 | 1.6 | 2.6 | 53.9 | 6.5 | 24.4 |
| II | 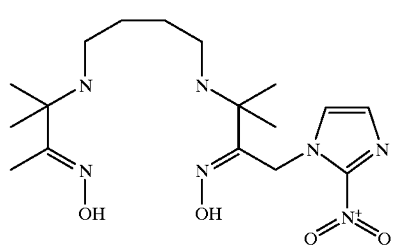 | 99 | 2 | 26.1 | 8.4 | 13.1 | 1.0 | 15.5 | 13.4 |
| | | | 60 | 6.6 | 1.3 | 1.4 | 34.1 | 11.4 | 40.0 |
| | | | 240 | 3.1 | 0.9 | 1.6 | 31.4 | 7.9 | 49.9 |
| VI | 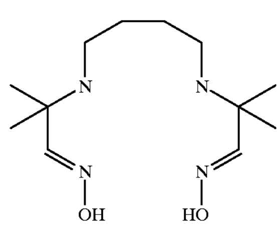 | 99 | 2 | 24.8 | 13.5 | 12.5 | 0.6 | 12.2 | 8.6 |
| | | | 60 | 13.4 | 5.3 | 10.4 | 34.6 | 13.7 | 16.3 |
| | | | 240 | 10.0 | 4.2 | 11.2 | 38.2 | 9.6 | 21.2 |

TABLE 2-continued

Rat Biodistribution

| Compound | Structure | RCP | Time | Muscle | Blood | Kidney | Bladder/Urine | Liver | Gut |
|---|---|---|---|---|---|---|---|---|---|
| VIII | 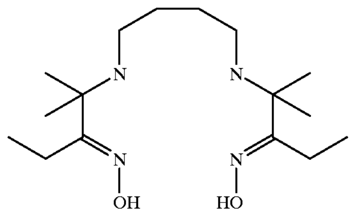 | 99 | 2 | 29.7 | 9.0 | 7.8 | 0.6 | 13.6 | 13.9 |
| | | | 60 | 7.4 | 1.8 | 2.5 | 32.2 | 13.1 | 36.2 |
| | | | 240 | 2.4 | 1.5 | 2.8 | 31.4 | 9.6 | 46.7 |
| III | 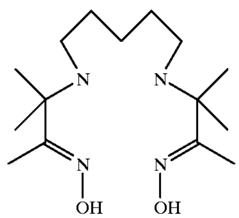 | 100 | 2 | 26.9 | 18.1 | 11.3 | 0.2 | 9.7 | 8.2 |
| | | | 60 | 10.1 | 1.1 | 4.2 | 51.8 | 5.4 | 25.0 |
| | | | 240 | 3.3 | 0.4 | 1.6 | 52.3 | 4.8 | 35.6 |
| IV | 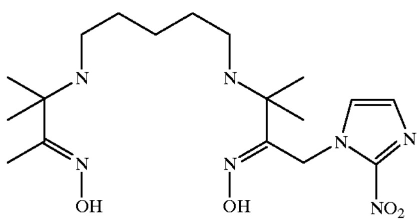 | 90 | 2 | 24.3 | 10.6 | 12.1 | 0.4 | 15.6 | 13.7 |
| | | | 60 | 8.2 | 1.0 | 2.7 | 29.5 | 2.5 | 50.9 |
| | | | 240 | 2.0 | 0.6 | 1.0 | 30.8 | 1.3 | 60.0 |
| X | 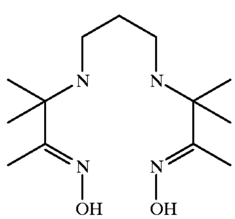 | 99 | 2 | 34.9 | 5.0 | 1.8 | 0.1 | 27.9 | 11.7 |
| | | | 60 | 7.9 | 6.8 | 2.1 | 9.5 | 13.1 | 51.5 |
| | | | 240 | 2.6 | 6.4 | 1.4 | 19.4 | 12.5 | 53.4 |
| V | 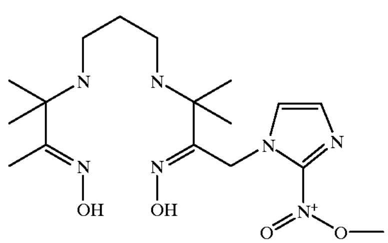 | 95 | 2 | 29.6 | 7.2 | 4.1 | 0.3 | 25.1 | 11.1 |
| | | | 60 | 4.2 | 4.2 | 3.2 | 12.0 | 21.5 | 45.9 |
| | | | 240 | 2.4 | 2.9 | 2.7 | 12.2 | 14.1 | 59.3 |
| VII | 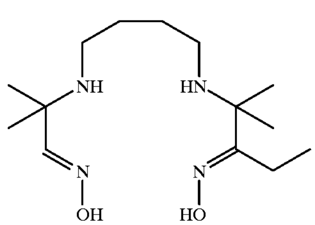 | 100 | 2 | 25.6 | 11.8 | 9.8 | 0.8 | 12.9 | 12.1 |
| | | | 60 | 9.2 | 3.0 | 3.4 | 40.8 | 11.6 | 23.2 |
| | | | 240 | 7.5 | 2.6 | 4.9 | 36.0 | 9.3 | 31.3 |

TABLE 2-continued
Rat Biodistribution
| Compound | Structure | RCP | Time | Muscle | Blood | Kidney | Bladder/Urine | Liver | Gut |
|---|---|---|---|---|---|---|---|---|---|
| IX | 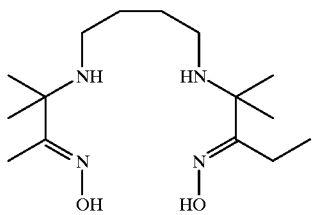 | 100 | 2 | 32.1 | 10.1 | 7.7 | 0.8 | 12.9 | 13.8 |
|  |  |  | 60 | 8.3 | 2.0 | 2.2 | 37.8 | 11.2 | 31.6 |
|  |  |  | 240 | 3.0 | 1.4 | 2.0 | 41.9 | 8.2 | 37.7 |
| H2dddo | 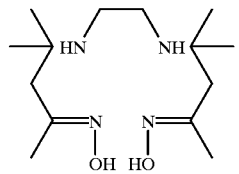 | 100 | 2 | 23.9 | 15.4 | 18.2 | 2.1 | 5.2 | 6.0 |
|  |  |  | 60 | 10.7 | 2.1 | 2.8 | 86.6 | 3.0 | 8.6 |
|  |  |  | 240 | 4.3 | 1.2 | 2.6 | 73.8 | 2.2 | 11.0 |
|  |  |  | 2 | 24.1 | 16.9 | 13.8 | 0.3 | 4.8 | 6.4 |
|  |  |  | 60 | 11.2 | 2.0 | 3.1 | 70.2 | 2.1 | 6.6 |
|  |  |  | 240 | 4.3 | 1.0 | 3.6 | 77.8 | 1.5 | 8.5 |
| XV | 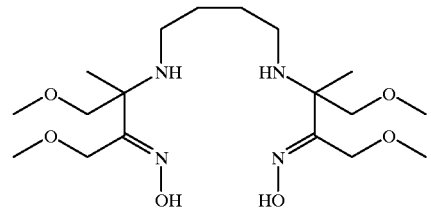 | 100 | 2 | 27.4 | 12.8 | 14.2 | 1.2 | 10.2 | 9.5 |
|  |  |  | 60 | 5.7 | 1.7 | 6.2 | 54.9 | 6.3 | 21.3 |
|  |  |  | 240 | 1.9 | 0.9 | 5.7 | 52.1 | 4.9 | 32.1 |
| XII | 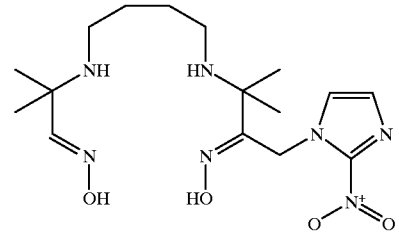 | 99 | 2 | 23.9 | 10.8 | 13.3 | 1.2 | 16.0 | 13.4 |
|  |  |  | 60 | 8.2 | 2.0 | 5.5 | 36.0 | 11.0 | 31.9 |
|  |  |  | 240 | 5.2 | 1.3 | 3.7 | 38.8 | 7.9 | 35.5 |
| XI | 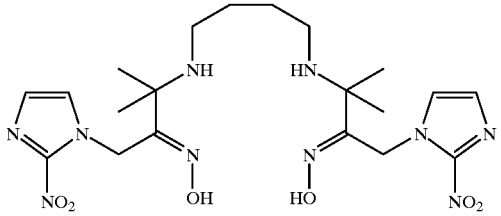 | 98 | 2 | 18.7 | 10.8 | 8.6 | 0.2 | 21.7 | 18.2 |
|  |  |  | 60 | 5.6 | 1.4 | 2.1 | 23.7 | 7.3 | 56.7 |
|  |  |  | 240 | 3.1 | 0.9 | 2.0 | 21.0 | 3.8 | 66.0 |
| XVI | 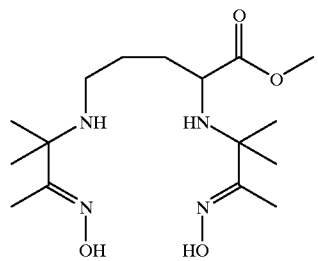 | 100 | 2 | 24.4 | 17.8 | 13.8 | 0.3 | 4.4 | 6.3 |
|  |  |  | 60 | 3.7 | 3.1 | 7.6 | 65.5 | 2.5 | 6.5 |
|  |  |  | 240 | 2.3 | 2.1 | 6.3 | 64.6 | 2.1 | 12.4 |

TABLE 2-continued

Rat Biodistribution

| Compound | Structure | RCP | Time | Muscle | Blood | Kidney | Bladder/Urine | Liver | Gut |
|---|---|---|---|---|---|---|---|---|---|
| XIII | 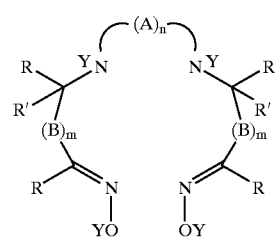 | 100 | 2 | 25.7 | 9.8 | 8.8 | 1.1 | 18.4 | 11.4 |
|  |  |  | 60 | 10.1 | 5.0 | 8.8 | 20.1 | 20.4 | 23.0 |
|  |  |  | 240 | 7.1 | 4.8 | 8.7 | 28.2 | 13.7 | 25.6 |

We claim:

1. A method for imaging of hypoxic tissue of a patient, which method comprises:
   (i) administering to said patient, an effective amount of a neutral radiometal complex of $^{99m}$Tc comprising $^{99m}$Tc and a ligand wherein said ligand does not carry a substituent which is a hypoxia-localizing moiety and said radiometal complex exhibits increased selective uptake in hypoxic tissue; and
   (ii) detecting the radioactive emissions from the radiometal complex wherein said ligand is where n=2–5;
   m=0, 1, 2;
   y is independently H or R;
   R, R' are independently: H, $C_{1-10}$ linear or branched hydrocarbon which may be alkyl or one or more of alkenyl; alkoxy; alkoxyalkyl, primary, secondary or tertiary amide; primary, secondary or tertiary amine; carboxylic acid; hydroxyalkyl; aryl; heterocyclic; heteroaryl or two R groups taken together with the atom(s) to which they are attached form a carbocyclic, heterocyclic, saturated or unsaturated spiro or fused ring; or the two R groups of a $CR_2$ or CRR' group adjacent to a NR group may be combined to give one or more —CONR— amide groups;
   A and B are the same or different and each is independently selected from the group consisting of —$CR_2$—, —CR=CR—, —N=N—, —NR—NR—, —N=CR— and —$CR_2$—Z—$CR_2$—, wherein Z is —O—, —S— or —NR— with the proviso that $(A)_n$ contains a backbone chain of five atoms or less and that $(B)_m$ contains a backbone chain of two atoms or less.

2. The method of claim 1 wherein said ligand is a substituted or unsubstituted diaminedioxime.

3. The method of claim 1 wherein the radiometal complex has the formula (TcOL), where L is the ligand.

4. The method of claim 1 wherein said ligand is

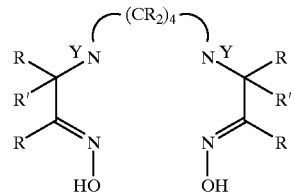

and where each of Y, R and R' is H or $C_{1-3}$ alkyl.

5. The method of claim 1 wherein said ligand is

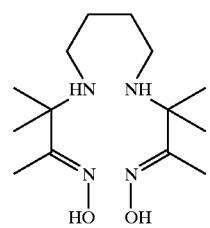

6. The method of claim 1 wherein said ligand is

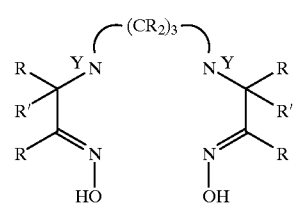

and where each of Y, R and R' is H or $C_{1-3}$ alkyl.

7. The method of claim 1 wherein said ligand is

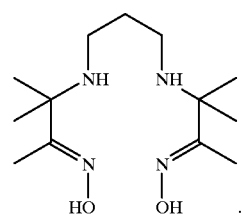

8. A method for radiotherapy of hypoxic tissue of a patient, which method comprises administering to said patient, an effective amount of a neutral radiometal complex of $^{99m}$Tc comprising $^{99m}$Tc and a ligand wherein said ligand does not carry a substituent which is a hypoxia-localizing moiety and said radiometal complex exhibits increased selective uptake in hypoxic tissue wherein said ligand is

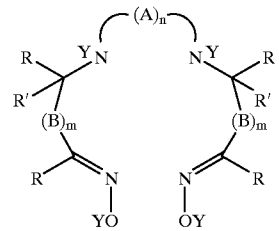

where n=2–5;
m=0, 1, 2;
y is independently H or R;

R, R' are independently: H, $C_{1-10}$ linear or branched hydrocarbon which may be alkyl or one or more of alkenyl; alkoxy; alkoxyalkyl; primary, secondary or tertiary amide; primary, secondary or tertiary amine; carboxylic acid; hydroxyalkyl; aryl; heterocyclic; heteroaryl or two R groups taken together with the atom(s) to which they are attached form a carbocyclic, heterocyclic, saturated or unsaturated spiro or fused ring; or the two R groups of a $CR_2$ or CRR' group adjacent to a NR group may be combined to give one or more —CONR— amide groups;

A and B are the same or different and each is independently selected from the group consisting of —$CR_2$—, —CR=CR—, —N=N—, —NR—NR—, —N=CR— and —$CR_2$—Z—$CR_2$—, wherein Z is —O—, —S— or —NR— with the proviso that $(A)_n$ contains a backbone chain of five atoms or less and that $(B)_m$ contains a backbone chain of two atoms or less.

9. The method of claim 8 wherein said ligand is a substituted or unsubstituted diaminedioxime.

10. The method of claim 8 wherein the radiometal complex has the formula (TcOL), where L is the ligand.

11. The method of claim 8 wherein said ligand is

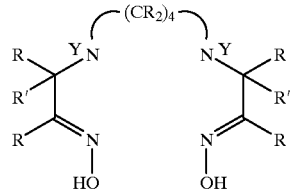

and where each of Y, R and R' is H or $C_{1-3}$ alkyl.

12. The method of claim 8 wherein said ligand is

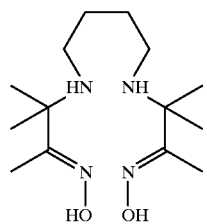

13. The method of claim 8 wherein said ligand is

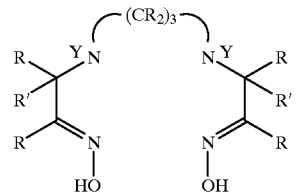

and where each of Y, R and R' is H or $C_{1-3}$ alkyl.

14. The method of claim 8 wherein said ligand is

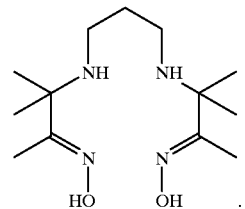

15. A radioimaging kit comprising a ligand which is

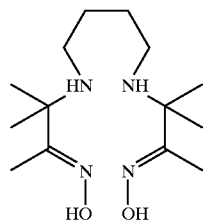

together with a stannous reducing agent and methylene diphosphonic acid in a freeze-dried state, which forms on the addition of $^{99m}$Tc-pertechnetate a complex for radioimaging.

16. The radioimaging kit of claim 15 which comprises a lyophilized mixture of the ligand of claim 15, methylene diphosphonic acid, stannous chloride, sodium hydrogen carbonate and sodium chloride.

* * * * *